US006924345B2

(12) United States Patent
Gagne et al.

(10) Patent No.: US 6,924,345 B2
(45) Date of Patent: Aug. 2, 2005

(54) PHOSPHORUS-CONTAINING COMPOSITIONS AND THEIR USE IN HYDROCYANATION, ISOMERIZATION AND HYDROFORMYLATION REACTIONS

(75) Inventors: Michel R. Gagne, Carrboro, NC (US); Kenneth G. Moloy, Hockessin, DE (US); Nora S. Radu, Landenberg, PA (US); Brian P. Santora, River Falls, WI (US); Wilson Tam, Boothwyn, PA (US)

(73) Assignee: Invista North America S.A R.L., Wilmington, DE (US)

( * ) Notice: Subject to any disclaimer, the term of this patent is extended or adjusted under 35 U.S.C. 154(b) by 146 days.

(21) Appl. No.: 10/659,205

(22) Filed: Sep. 10, 2003

(65) Prior Publication Data

US 2004/0054105 A1 Mar. 18, 2004

Related U.S. Application Data

(62) Division of application No. 09/994,135, filed on Nov. 26, 2001, now Pat. No. 6,660,876.

(51) Int. Cl.[7] ............................................. C08F 130/02
(52) U.S. Cl. ...................................... 526/274
(58) Field of Search ......................... 526/274

(56) References Cited

U.S. PATENT DOCUMENTS

| | | | |
|---|---|---|---|
| 3,496,215 A | 2/1970 | Drinkard et al. | |
| 3,496,217 A | 2/1970 | Drinkard et al. | |
| 3,631,191 A | 12/1971 | Kane et al. | |
| 3,655,723 A | 4/1972 | Drinkard et al. | |
| 3,766,237 A | 10/1973 | Chia et al. | |
| 3,846,461 A | 11/1974 | Shook, Jr. | |
| 3,847,959 A | 11/1974 | Shook, Jr. et al. | |
| 3,903,120 A | 9/1975 | Shook, Jr. et al. | |
| 3,907,847 A | 9/1975 | Keblys | |
| 4,668,651 A | 5/1987 | Billig et al. | |
| 4,769,498 A | 9/1988 | Billig et al. | |
| 4,874,884 A | 10/1989 | McKinney et al. | |
| 5,210,260 A | 5/1993 | Bohshar et al. | |
| 5,235,113 A | 8/1993 | Sato et al. | |
| 5,432,289 A | 7/1995 | Pugin et al. | |
| 5,512,696 A | 4/1996 | Kreutzer et al. | |
| 5,523,453 A | 6/1996 | Breikss | |
| 5,543,536 A | 8/1996 | Tam | |
| 5,688,986 A | 11/1997 | Tam et al. | |
| 5,693,843 A | 12/1997 | Breikss et al. | |
| 5,710,306 A | 1/1998 | Snijder et al. | |
| 5,723,641 A | 3/1998 | Tam et al. | |
| 5,817,850 A | 10/1998 | Pastor et al. | |
| 5,821,378 A | 10/1998 | Foo et al. | |
| 5,910,600 A | 6/1999 | Urata et al. | |
| 5,959,135 A | 9/1999 | Garner et al. | |
| 5,981,772 A | * 11/1999 | Foo et al. ............... | 549/349 |
| 5,990,318 A | 11/1999 | Chan et al. | |
| 6,031,120 A | 2/2000 | Tam | |
| 6,069,267 A | 5/2000 | Tam | |
| 6,120,700 A | * 9/2000 | Foo et al. ............... | 252/182.3 |
| 6,121,184 A | 9/2000 | Druliner et al. | |
| 6,127,567 A | * 10/2000 | Garner et al. ........... | 558/338 |
| 6,171,996 B1 | 1/2001 | Garner et al. | |
| 6,242,633 B1 | 6/2001 | Fischer et al. | |
| 6,265,620 B1 | 7/2001 | Urata et al. | |
| 6,355,833 B2 | 3/2002 | Fischer et al. | |
| 2001/0014647 A1 | 8/2001 | Basf | |
| 2002/0128501 A1 | * 9/2002 | Zhang ..................... | 556/9 |

FOREIGN PATENT DOCUMENTS

| | | |
|---|---|---|
| CN | 1292728 | 3/1991 |
| CN | 1304334 | 7/2001 |
| EP | 0864577 | 9/1998 |
| EP | 0877029 | 11/1998 |
| WO | WO93 03839 | 3/1993 |
| WO | WO95 30680 | 11/1995 |
| WO | WO96 22968 | 8/1996 |
| WO | WO 97/33854 | 9/1997 |
| WO | WO98 12202 | 3/1998 |
| WO | WO98 43935 | 10/1998 |
| WO | WO99 06146 | 2/1999 |
| WO | WO99 13983 | 3/1999 |
| WO | WO99 46044 | 9/1999 |
| WO | WO99 62855 | 12/1999 |
| WO | WO99 64155 | 12/1999 |
| WO | WO 01/21580 | 3/2001 |

OTHER PUBLICATIONS

Bayston, Daniel J. et al., Preparation and Use of a Polymer Supported BINAP Hydrogenation Catalyst, J. Org. Chem. 1998, vol. 63, pp. 3137–3140.

Nozaki, Kyoko et al., Asymmetric Hydroformylation of Olefins in a Highly Cross–Linked Polymer Matrix, J. Am. Chem. Soc., 1998, vol. 120, pp. 4051–4052.

Brunkan, Nicole M. et al., Effect of Chiral Cavities Associated with Molecularty Imprinted Platinum Centers on the Selectivity of Ligand–Exchange Reactions at Platinum, J. Am. Chem. Soc., 2000, vol. 122, pp. 6217–6225.

Annex Form PCT/ISA/206 Communication Relating to the Results of the Partial International Search, International Application No. PCT/US02/37304, filed Nov. 20, 2002.

Comprehensive Organometallic Chemistry, ED: G. Wilkinson, F. g. A. Stone, and E. W. Abel, New York: Pergamon Press 1982, Chapter 55.

(Continued)

Primary Examiner—Bernard Lipman

(57) ABSTRACT

A polymeric, phosphorus-containing composition made by heating, in the presence of an initiator, preferably a free radical initiator, and optionally in the presence of one or more comonomers, at least one substituted phosphonylated 2,2'-dihydroxyl-1,1'-binaphthalene or at least one substituted 2,2'-dihydroxyl-1,1'-biphenylene.

3 Claims, No Drawings

OTHER PUBLICATIONS

Richard Heck, Organic Reactions, 1982, Chapter 2, pp. 348.

Parrinello et al., J. Org. Chem. 1986, Platinum–Catalyzed Asymmetric Hydroformylation with a Polymer–Attached Optically Active Phosphine Ligand, vol. 51, pp. 4189–4195.

Gloede et al., Z. Anorg. Allg. Chem., 1986, Zur Halogenierung der o–Methoxphenylester von $P^{111}$–Sauren, vol. 535, 221–228.

Machon et al, Synthesis 1988, Synthesis of Fuor[3,4,-α] pyrimidine Derivatives via Reaction of 4–Methylpyrimidine–5–carboxylic Acids with Thionyl Chloride, vol., 2, pp. 142–144.

Baker et al., J. Chem. Soc. Chem. Commun. 1991, Chiral Aryl Diphosphites: a New Class of Ligands for Hyrocyanation Catalysis, pp. 1292–1293.

Baker et al. J. Chem. Soc. Chem. Commun. 1991, Chelating Diphosphite Complexes of Nickel(0) and Platinum (0): Their Remarkable Stability and Hydrocyanation Activity, pp. 803–805.

Perich et al., Aust. J. Chem., 1991, Synthesis of Casein–Related Peptides and Phosphopeptides. VII* The Efficient Synthesis of Ser(P)–Containing Peptides by the Use of Boc–Ser($PO_3R_2$)–OH Derivatives, vol. 44, pp. 233–252.

Jongsma et al. Polymer, 1992, A New Type of Highly Active Polymer–Bound Rhodium Hydroformylation Catalyst, vol. 33, No. 1, pp. 161–165.

Helinski et al., Tet. Lett., 1993, New Phosphitylating Reagent in the Nucleotide Chemistry Containing Two 4–Nitrophenoxy Leaving Groups. Remarkably Fast and Clean Phosphitylations Activatedby DBU Leading to Thio- and Seleno–oligonucleotides, vol. 34, No. 40, pp. 6451–6454.

Piet et al, Macromol. Symp, 1994, Polymer–Bound Bulky–Phosphite Modified Rhodium Hydroformylation Catalysts, vol. 80, 241–256.

Cabri et al., Acc. Chem. Res., 1995, Recent Developments and New Perspectives in the Heck Reaction, vol. 28, pp. 2–7.

Schlick et al., Acta Polymer, 1996, Catalysis on polymer supports, vol. 47, pp. 1–15.

Moroz et al., J. Mol. Catal. A, 1996, Heterogenized Catalysts for Olefin Hydroformylation Containng Cobalt and Palladium–Cobalt Complexes Anchored on Phosphinated $SiO_2$: a $^{13}C$ Solid–State NMR Study, Chemical 112, pp. 217–233.

Behringer et al., J. Chem. Soc., Chem. Commun., 1996, Immobilization and Chelation of Metal Complexes with Bifunctional Phosphine Ligands: A Solid–State NMR Study, pp. 653–654.

Bayston et al., J. Org. Chem. 1998, Preparation and Use of a Polymer Supported BINAP Hydrogenation Catalyst, vol. 63, pp. 3137–3140.

Nozaki, Kyoko et al., Asymmetric Hydroformylation of Olefins in a Highly Cross–Linked Polymer Matrix, J. Am. Chem. Soc., 1998, vol. 120, pp. 4051–4052.

Nozaki et al., Bull. Chem,. Soc. Jpn. 1999, Asymmetric Hydroformylation of Olefins in Highly Crosslinked Polymer Matrixes, vol. 72, pp. 1911–1918.

Brunkan, Nicole M. et al., Effect of Chiral Cavities Associated with Molecularly Imprinted Platinum Centers on the Selectivity of Ligand–Exchange Reactions at Platinum, J. Am. Chem. Soc., 2000, vol. 122, pp. 6217–6225.

* cited by examiner

PHOSPHORUS-CONTAINING COMPOSITIONS AND THEIR USE IN HYDROCYANATION, ISOMERIZATION AND HYDROFORMYLATION REACTIONS

CROSS REFERENCE TO RELATED APPLICATIONS

This application is a divisional of application Ser. No. 09/994,135, U.S. Pat. No. 6,660,876 filed Nov. 26, 2001.

BACKGROUND OF THE INVENTION

1. Field of the Invention

The present invention relates to ethylenically unsaturated, phosphorus-containing, bidentate ligands (monomers) and polymeric derivatives thereof as well as polymeric precursors to said polymeric derivatives and methods of making the same. The present invention also relates to catalyst compositions involving a Group VIII metal in the presence of the polymeric bidentate ligands and use of such catalysts in hydrocyanation, isomerization, and hydroformylation reactions.

2. Description of the Related Art

Phosphorus-based ligands are generally known in catalysis, finding use for a number of commercially important chemical transformations. Phosphorus-based ligands commonly encountered in catalysis include phosphines, phosphinites, phosphonites and phosphites. Monodentate phosphorus ligands, e.g. monophosphine and monophosphite ligands, are compounds that usually contain a single phosphorus atom that serves as an electron donor to a transition metal. Bidentate phosphorus ligands, e.g. bisphosphine, bisphosphinite, bisphosphonite, bisphosphite, and bis(phosphorus) ligands, in general, contain two phosphorus electron donor atoms and typically form cyclic chelate structures with transition metals.

Two particularly important industrial processes using phosphorus ligands as catalysts are olefin hydrocyanation and isomerization of branched nitriles to linear nitriles. Phosphite and phosphinite ligands are particularly good ligands for both reactions. The hydrocyanation of ethylenically unsaturated compounds (olefins) using transition metal complexes with monodentate phosphite ligands is well documented in the prior art. See, for example, U.S. Pat. Nos. 3,496,215; 3,631,191; 3,655,723; 3,766,237 and 5,543,536. Bidentate phosphite ligands have also been shown to be particularly useful ligands in the hydrocyanation of activated ethylenically unsaturated compounds. See, for example, J. Chem. Soc., Chem. Commun., 1991, 1292; J. Chem. Soc., Chem. Commun., 1991, 803; PCT Pat. App. WO 9303839; U.S. Pat. Nos. 5,512,696; 5,723,641; and 5,688,986. Bidentate phosphinite and phosphonite ligands are described in U.S. Pat. Nos. 5,817,850; 5,523,453; 5,693,843; and PCT Pat. App. WO 9964155, WO 9913983, WO 9946044, and WO 9843935.

Hydroformylation is another industrially useful process that utilizes catalysts made from phosphorus-containing ligands. The use of phosphine ligands, including diphosphines, is known for this purpose. The use of catalysts made from phosphite ligands is also known. Such catalysts usually contain a Group VIII metal, as described in, for example, U.S. Pat. No. 5,235,113.

Recovery of the ligand and catalyst is important for a successful commercial process. Typical separation procedures to remove the product(s) from the catalyst and ligand involve extraction with an immiscible solvent or distillation. It is usually difficult to recover the catalyst and ligand quantitatively. For instance, distillation of a volatile product from a non-volatile catalyst results in thermal degradation of the catalyst. Similarly, extraction results in some loss of catalyst into the product phase. For extraction, one would like to be able to select and/or control the solubility of the ligand and catalyst to disfavor solubility in the product phase. These ligands and metals are often very expensive and thus it is important to keep such losses to a minimum for a commercially viable process.

One method to solve the problem of catalyst and product separation is to attach the catalyst to an insoluble support. Examples of this approach have been previously described, and general references on this subject can be found in "Supported Metal Complexes: A New Generation of Catalysts", F. R. Hartley and D. Boston, Reidel Publishing, 1985; Acta Polymer., 1996, 47, 1; "Comprehensive Organometallic Chemistry", Ed: G. Wilkinson, F. G. A. Stone, and E. W. Abel, New York: Pergamon Press, 1982, Chapter 55, "Polymer Supported Catalysts"; J. Mol. Catal. A, 1995, 104, 17; and Macromol. Symp., 1994, 80, 241. Specifically, monophosphine and monophosphite ligands attached to solid supports are described in these references. Bisphosphine ligands have also been attached to solid supports and used for catalysis, as described in, for example, U.S. Pat. Nos. 5,432,289 and 5,990,318; J. Mol. Catal. A, 1996, 112, 217, J. Chem. Soc., Chem. Commun., 1996, 653; J. Org. Chem., 1998, 63, 3137; Spec. Chem., 1998, 18, 224 and PCT Pat. App. WO 9812202. PCT Pat. Apps. WO 9906146 and WO 9962855 show use of supported phosphorus ligands in hydrocyanation and hydroformylation reactions, respectively. Bisphosphite ligands have also been grafted to solid supports such as those described in U.S. Pat. No. 6,121,184. The solid support in these prior art examples can be organic, e.g., a polymer resin, or inorganic in nature.

Polymer-supported multidentate phosphorus ligands may be prepared by a variety of methods known in the art, as described in U.S. Pat. Nos. 4,769,498 and 4,668,651, PCT Pat. App. WO 9303839 and WO 9906146, and European Pat. Apps. EP 0864577 A2 and EP 0877029 A2. The prior art discloses side-chain polymers containing multidentate phosphorus ligands as pendant groups.

Another method to solve the problem of separating the catalyst from the reaction product is to copolymerize phosphorus-containing ligands with other non-ligand monomers to produce insoluble phosphorus-containing ligands. Examples of such polymer-immobilized phosphine ligands have been reported in J. Am. Chem. Soc., 2000, 122, 6217 and J. Org. Chem., 1986, 51, 4189. In addition, polymer-immobilized phosphine-phosphite ligands and their use in hydroformylation catalysis have recently been described in Bull. Chem. Soc. Jpn., 1999, 72, 1911; J. Am. Chem. Soc., 1998, 120, 4051; and European Pat. App. EP 0864577.

To address the important issue of ligand recovery, this invention provides novel monomeric bidentate ligands and a method for their synthesis, polymeric bidentate ligands prepared from the monomeric ligands and a method for their synthesis, monomeric or polymeric phosphorus-containing compositions that may be combined with a Group VIII metal, and the use of this monomeric or polymeric phosphorus-containing composition combined with a Group VIII metal to act as a catalyst in reactions for hydrocyanation, hydroformylation, and isomerization. The polymeric, phosporus-containing catalyst composition is readily recoverable from the reaction products.

BRIEF SUMMARY OF THE INVENTION

In its first aspect, the present invention provides novel, phosphorus-containing bidentate ligand (monomer) compounds as shown in Formula I or as shown in Formula II, substituted with a vinyl group and/or an acrylate group [e.g. ethenyl ($CH_2$=CH—), propenyl (($CH_3$)(H)C=CH—), acryloyl ($CH_2$=CH—C(O)—O—), or methacryloyl ($CH_2$=C($CH_3$)—C(O)—O—)]:

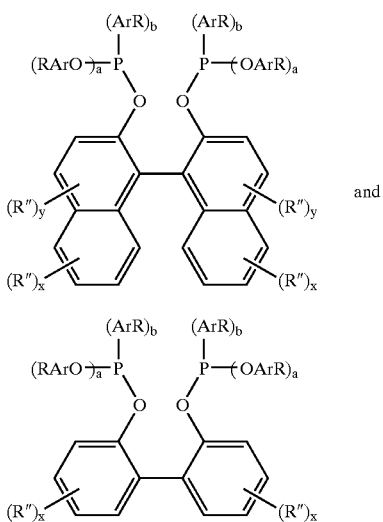

wherein:
x=0 to 4;
y=0 to 2;
a and b individually are either 0, 1, or 2, provided a+b=2;

each Ar is individually phenyl or naphthyl, and the two Ar groups that are directly or indirectly (through an oxygen) bonded to the same phosphorus atom may be linked to each other by a linking unit selected from the group consisting of direct bond, alkylidene, secondary or tertiary amine, oxygen, sulfide, sulfone, and sulfoxide;

each R is individually hydrogen, ethenyl, propenyl, acryloyl, methacryloyl, an organic radical with a terminal ethenyl, propenyl, acryloyl, or methacryloyl group, linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether;

each Ar can be further substituted with linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether;

each R" is individually hydrogen, ethenyl, propenyl, an organic radical with a terminal ethenyl or propenyl group, linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether;

provided at least one R represents ethenyl, propenyl, acryloyl, methacryloyl or the organic radical with a terminal ethenyl, propenyl, acryloyl, or methacryloyl group or at least one R" represents ethenyl, propenyl, or the organic radical with a terminal ethenyl or propenyl group.

Preferred are compounds of Formula I wherein a=2, b=0, R is primary or secondary alkyl located ortho to the oxygen bonded to Ar, wherein y≧1, and wherein at least one R" is primary or secondary alkyl group and is located at the ortho position of the oxygen bonded to the binaphthalene group, or a compound of Formula II wherein a=2, b=0, R is primary or secondary alkyl located ortho to the oxygen bonded to Ar, wherein x≧1 and wherein at least one R" is primary or secondary alkyl group and is located at the ortho positions of the oxygen bonded to the biphenylene group.

In its second aspect, the invention is a process for preparing certain phosphorus-containing bidentate ligand (monomer) compounds of Formula I, wherein a is 1 or 2 and b is 0 or 1 with the condition that a+b=2, or certain compounds of Formula II, wherein a is 1 or 2 and b is 0 or 1 with the condition that a+b=2. The process comprises:

(1) reacting at least one of acryloyl chloride or methacryloyl chloride with a polyhydric alcohol to make at least one of monoacrylate or monomethacrylate, (2) reacting at least one of the monoacrylate or monomethacrylate with at least one of phosphorus trichloride or phosphorodichloridite or aryldichlorophosphine ($Cl_2P$—Ar) to give at least one of phosphorochloridite- or aryl, aryloxychlorophosphinite-containing acrylate or methacrylate, (3) reacting at least one of the phosphorochloridite- or aryl,aryloxychlorophosphinite-containing acrylate and/or methacrylate from step (2) with at least one compound of Formula III and/or at least one compound of Formula IV,

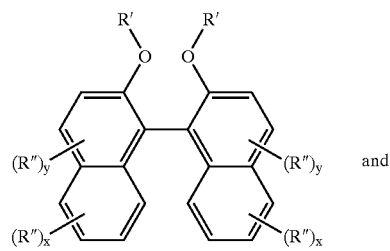

wherein:
x=0 to 4;
y=0 to 2;
each R' individually is hydrogen or M, wherein M is an alkali metal or an alkaline earth metal, each R" is individually hydrogen, ethenyl, propenyl, an organic radical with a terminal ethenyl or propenyl group, linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether.

Preferred are compounds of Formula III wherein a=2, b=0, R is primary or secondary alkyl located ortho to the oxygen bonded to Ar, wherein y≧1, and wherein at least one R" is primary or secondary alkyl group and is located at the ortho position of the oxygen bonded to the binaphthalene group, or a compound of Formula IV wherein a=2, b=0, R is primary or secondary alkyl located ortho to the oxygen bonded to Ar, wherein x≧1 and wherein at least one R" is primary or secondary alkyl group and is located at the ortho positions of the oxygen bonded to the biphenylene group.

In its third aspect, the present invention provides a method for making a polymeric, phosphorus-containing composition by heating, in the presence of an initiator, preferably a free radical initiator, and optionally in the presence of a Group VIII metal, a composition comprising at least one compound of Formula I and/or at least one compound of Formula II, provided at least one R represents ethenyl, propenyl, acryloyl, methacryloyl or the organic radical with a terminal ethenyl, propenyl, acryloyl, or methacryloyl group or at least one R" represents ethenyl, propenyl, or the organic radical with a terminal ethenyl or propenyl group.

In its fourth aspect, the present invention also provides a polymeric, phosphorus-containing composition made as described above in aspect three.

In its fifth aspect, the present invention also provides a method for producing a polymeric phosphorus-containing composition made by:

(1) heating in the presence of an initiator a composition comprising at least one compound of Formula III and/or at least one compound of Formula IV,

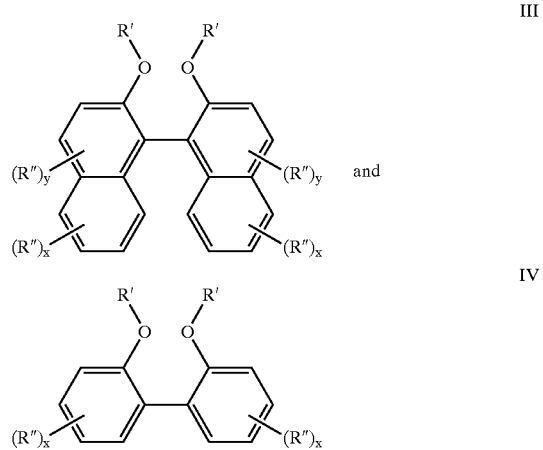

wherein:
x=0 to 4;
y=0 to 2;
each R' individually is hydrogen, an alkali metal, an alkaline earth metal or a hydroxyl-protective group selected from alkyl, alkoxyalkyl (e.g., $CH_3OCH_2$—), carbonylalkyl (e.g., $CH_3$—C(O)—), and a crown ether formed by taking both R' groups together;

each R" is individually hydrogen, ethenyl, propenyl, an organic radical with a terminal ethenyl or propenyl group, linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether;

provided at least one R" represents ethenyl, propenyl, or the organic radical with a terminal ethenyl or propenyl group;

by contacting the composition with an initiator, preferably a free radical initiator, and heating to a preselected temperature for a period of time sufficient to permit reaction, and (2) phosphonylating the resulting polymer.

Preferred are compounds of Formula III wherein a=2, b=0, R is primary or secondary alkyl located ortho to the oxygen bonded to Ar, wherein y≧1, and wherein at least one R" is primary or secondary alkyl group and is located at the ortho position of the oxygen bonded to the binaphthalene group, or a compound of Formula IV wherein a=2, b=0, R is primary or secondary alkyl located ortho to the oxygen bonded to Ar, wherein x≧1 and wherein at least one R" is primary or secondary alkyl group and is located at the ortho positions of the oxygen bonded to the biphenylene group.

In its sixth aspect, the present invention further provides a polymer composition made as described above in aspect five.

In its seventh aspect, the present invention further provides a method to produce a polymeric, phosphorus-containing composition by heating a phosphorochloridite containing at least one acrylate or methyl acrylate group in the presence of an initiator, preferably a free radical initiator, to produce a polymer containing phosphorochloridite, and further reacting this polymer with at least one compound of Formula III and/or Formula IV wherein each R' individually is H or M, with the provision that if R' is protected, the protecting group must be removed before reacting the compound of Formula III and/or Formula IV with the polymer containing phosphorochloridite.

In its eighth aspect, the present invention further provides a polymer composition made as described above in aspect seven.

In its ninth aspect, the present invention further provides a catalyst composition comprising at least one monomeric, phosphorus-containing composition of aspect one and at least one Group VIII metal, and/or at least one polymeric, phosphorus-containing composition of aspect four and/or aspect six and/or aspect eight and at least one Group VIII metal, and/or at least one polymeric, phosphorus-containing, catalyst material of aspect three wherein the polymerization was carried out in the presence of at least one Group VIII metal.

In its tenth aspect, the present invention further provides the use of any of the present catalyst compositions for a hydrocyanation process comprising reacting an unsaturated organic compound with HCN in the presence of the catalyst composition, with or without a Lewis Acid.

In its eleventh aspect, the present invention further provides the use of any of the present catalyst compositions for an isomerization process comprising reacting an unsaturated organic nitrile compound in the presence of the catalyst composition.

In its twelfth aspect, the present invention further provides the use of any of the present catalyst compositions for a hydroformylation process comprising reacting an unsaturated organic compound with CO and $H_2$ in the presence of the catalyst composition.

DETAILED DESCRIPTION OF THE INVENTION

The phosphorus-containing compositions of the present invention may be viewed as belonging to the family of bidentate ligands, because each pair of trivalent phosphorus atoms are potentially available to simultaneously coordinately bond to a single Group VIII metal atom; i.e., the phosphorus atoms represent electron donors to the same metal atom of the resulting metal complex.

In each case, one of the phosphorus to oxygen bonds is associated with the oxygen of the hydroxyl group of a 2,2'-dihydroxyl-1,1'-binaphthalene or 2,2'-dihydroxyl-1,1'-biphenylene structure. The two other bonds associated with the trivalent phosphorus involve a pair of phosphorus to aryl carbon bonds, a pair of phosphorus to aryloxy oxygen bonds, or one phosphorus to aryl carbon bond and one phosphorus to aryloxy oxygen bond. Each aryl (Ar) or aryloxy (—O—Ar) may be phenyl, naphthyl, substituted phenyl, or substituted naphthyl. Two Ar groups that are directly or indirectly (through an oxygen) bonded to the same phosphorus atom may be linked to each other by a linking unit selected from the group consisting of direct bond, alkylidene, secondary or tertiary amine, oxygen, sulfide, sulfone, and sulfoxide.

The phosphorus-containing bidentate ligand (monomer) compounds represented by Formulas I and II comprise bidentate phosphites (compounds of Formula I or II having three phosphorus to oxygen bonds), phosphinites (compounds of Formula I or II having one phosphorus to oxygen bond and two phosphorus to carbon bonds), phosphonites (compounds of Formula I or II having two phosphorus to oxygen bonds and one phosphorus to carbon bond), and mixed phosphite/phosphinites, phosphite/phosphonites, phosphinite/phosphonites.

The bidentate phosphites (those compounds of Formula I or II having three phosphorus to oxygen bonds) of the present invention can be prepared as described in European Pat. App. 92109599.8 of Mitsubishi Kasei Corporation and the corresponding U.S. Pat. No. 5,235,113, incorporated herein by reference. The reaction of a phosphorochloridite with a binaphthol represented by Formula III wherein R' is H or M will lead to a bidentate phosphite represented by Formula I. Similarly, the reaction of a phosphorochloridite with a biphenol represented by Formula IV wherein R' is H or M will lead to a bidentate phosphite represented by Formula II. U.S. Pat. Nos. 6,031,120 and 6,069,267 (incorporated herein by reference) describe selective synthesis of bidentate phosphite compounds. For example, the phosphorochloridite can be prepared in-situ from phosphorus trichloride and a phenol such as o-cresol and then treated in the same reaction vessel with an aromatic diol to give the bidentate phosphite. When R' is H, it is preferred to have a stoichiometric excess of a base present during the phosphonylation to drive the reaction by salt formation with hydrogen chloride being inherently co-produced. Preferably the base is a trialkylamine. More preferably, the trialkylamine is one with $C_1$ to $C_{12}$ branched or straight chain alkyl groups. Most preferred is triethylamine.

The bidentate phosphinite compounds of the present invention (those compounds of Formula I and Formula II having one phosphorus to oxygen bond and two phosphorus to carbon bonds) and bidentate phosphonite compounds (those compounds of Formula I and Formula II having two phosphorus to oxygen bonds and one phosphorus to carbon bond) may be synthesized by phosphonylation of structures represented by Formulas III and IV with diarylchlorophosphine and ClP(Ar)(—O—Ar) respectively. See, for example, U.S. Pat. No. 5,523,453, incorporated herein by reference, which describes preparation of bidentate phosphinites.

Alternatively, the phosphonylation reaction can be carried out by a process as described in U.S. Pat. No. 5,910,600. The first step is to convert the phenolic groups of the substituted binaphthol and/or substituted biphenol to —OM groups, wherein M is an alkali metal or an alkaline earth metal, followed by treatment with the phosphonylating agent such as phosphorochloridite to give the organodiphosphite compound.

The second aspect of the invention is a process for preparing certain phosphorus-containing bidentate ligand (monomer) compounds comprising those compounds of Formula I, wherein a is 1 or 2 and b is 0 or 1 with the condition that a+b=2, or those compounds of Formula II, wherein a is 1 or 2 and b is 0 or 1 with the condition that a+b=2, said process comprising:

(1) reacting at least one of acryloyl chloride or methacryloyl chloride with a polyhydric alcohol to make at least one of monoacrylate or monomethacrylate, (2) reacting at least one of the monoacrylate or monomethacrylate with at least one of phosphorus trichloride or phosphorodichloridite or aryldichlorophosphine ($Cl_2P$—Ar) to give at least one of phosphorochloridite- or aryl, aryloxychlorophosphinite-containing acrylate or methacrylate, (3) reacting at least one of the phosphorochloridite- or aryl, aryloxychlorophosphinite-containing acrylate and/or methacrylate from step (2) with at least one compound of Formula III and/or at least one compound of Formula IV, wherein each R' individually is hydrogen or M, wherein M is an alkali metal or an alkaline earth metal.

The term "polyhydric alcohol" used herein refers to, unless otherwise indicated, a molecule having two or more hydroxyl groups. Each hydroxyl group is attached to an aromatic ring, $Ar^2$, wherein each $Ar^2$ is independently selected from the group consisting of $C_6$ to $C_{40}$ phenylene, $C_{10}$ to $C_{40}$ naphthylene, and combinations thereof. Examples of polyhydric alcohols include, but are not limited to, those illustrated below:

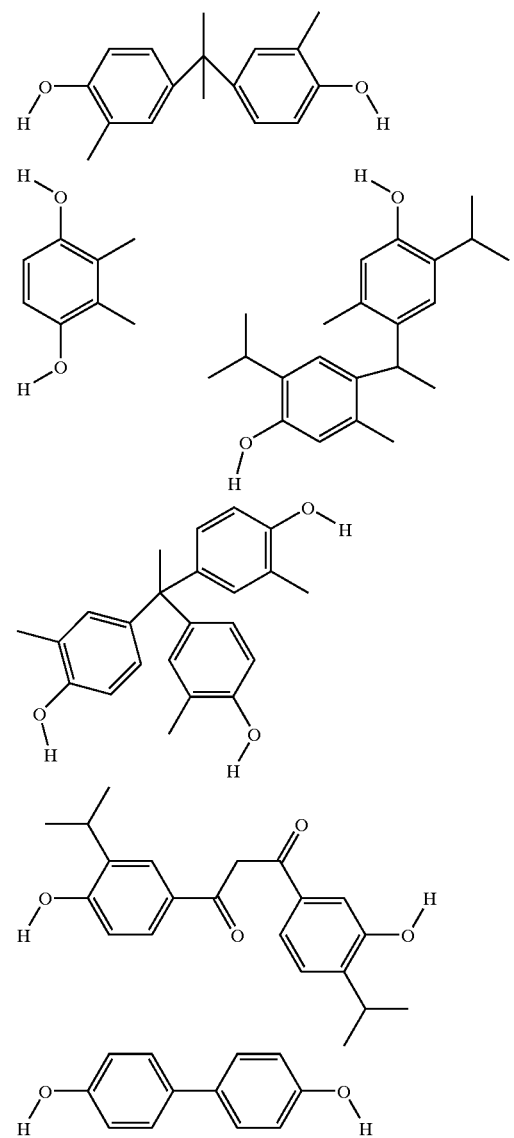

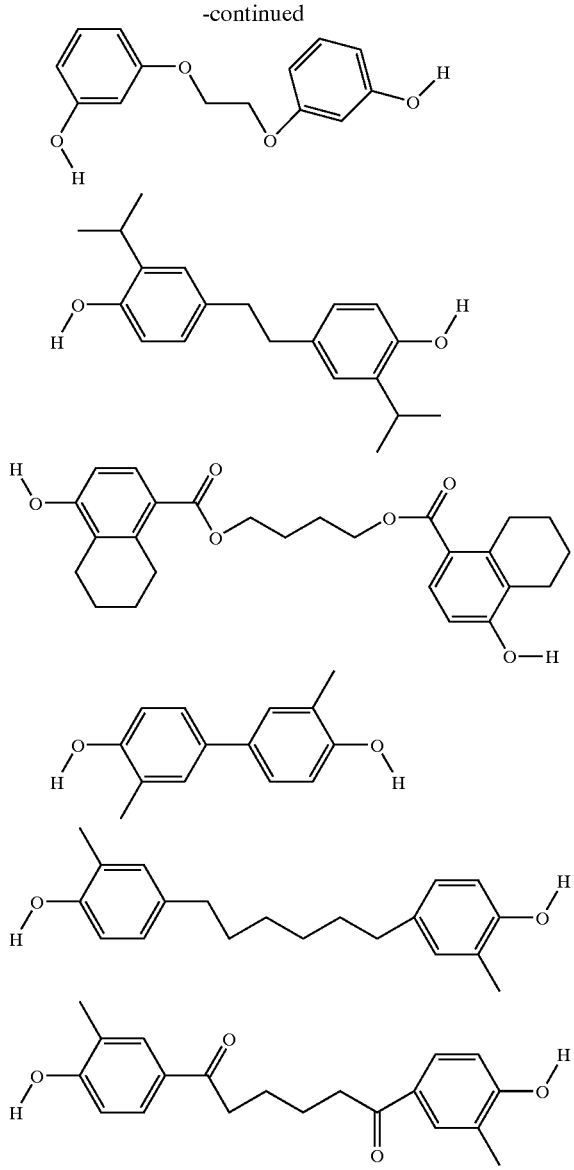

The preferred polyhydric alcohol is a diol wherein each hydroxyl is attached to an aromatic group selected from the group consisting of phenylene and naphthylene and the aromatic group is further substituted with a primary alkyl or secondary alkyl or cycloalkyl group ortho to the oxygens.

The polyhydric alcohol is contacted with acryloyl chloride or methacryloyl chloride to generate a solution containing acrylates or methacrylates. Depending on the structure of the polyhydric alcohol, di-, tri-, and higher order acrylates and methacrylates can be generated. An organic base such as trialkylamine is used to react with the resultant HCl. The mixture can be purified by methods known in the art; for example, column chromatography can be used. The acrylate or methacrylate has one or more reactive aromatic alcohol groups that can react with phosphorodichloridite or phosphorus trichloride or aryl dichlorophosphine or mixture thereof to form phosphorochloridite or diaryl chlorophosphine or mixture thereof. The preferred phosphorodichloridite has the formula selected from the group consisting of $Cl_2P(O—Ar—R)$, wherein the R group is preferably ortho to the oxygen. The most preferred phosphorodichloridites are those derived from phenols containing one ortho substituent that is primary or secondary alkyl or cycloalkyl of 1 to 12 carbon atoms.

The use of mixtures of $ClP(Ar)(—O—Ar)$ and diarylchlorophosphine with an aromatic diol will give a bidentate phosphorus compound with both phosphonite and phosphinite groups. The use of mixtures of phosphorochloridite and diarylchlorophosphine with an aromatic diol will give a bidentate phosphorus compound with both phosphite and phosphinite groups. The use of mixtures of phosphorochloridite and $ClP(Ar)(—O—Ar)$ will give a bidentate phosphorus compound with both phosphite and phosphonite groups.

Typically the pair of trivalent phosphorus atoms is incorporated into the bidentate ligand moiety (i.e., into a compound of Formula I or Formula II) by reacting a diarylchlorophosphonite $(ClP(Ar)_2)$, diaryloxychlorophosphonite $(ClP(—O—Ar)_2)$, an aryl,aryloxychlorophosphinite $(ClP(Ar)(—O—Ar))$ or the like with the hydroxyl groups of a 2,2'-dihydroxyl-1,1'-binaphthalene or a 2,2'-dihydroxyl-1,1'-biphenylene structure. As such, any protected diol structure is converted (e.g., hydrolyzed, protonated, or the like) back to the hydroxyl group prior to phosphonylation. Preferably the phosphonylation reaction [producing what is referred to herein as a diaryloxyphonite unit $(—P(—O—Ar)_2)$, a diarylphosphine unit $(—P(Ar)_2)$, or aryl,aryloxyphosphinite unit $(—P(Ar)(—O—Ar))$ or mixture thereof] is performed with at least one stoichiometric equivalent of the diarylchlorophosphonite $(ClP(Ar)_2)$, or diaryloxychlorophosphonite $(ClP(—O—Ar)_2)$, or aryl,aryloxychlorophosphinite $(ClP(Ar)(—O—Ar))$ or mixture thereof for each hydroxyl in the diol structure. Advantageously, a stoichiometric excess of a trialkylamine or the like is present during the phosphonylation to drive the reaction by salt formation with hydrogen chloride being inherently co-produced. Again the aryl (Ar) is selected from the group consisting of phenyl, naphthyl, substituted phenyl, and substituted naphthyl with the proviso that, for any individual phosphorus, the pair of aryls or aryloxys or combination of aryl and aryloxy may optionally be linked to each other either directly or through a linking unit. When the aryl is a substituted phenyl or naphthyl, the substitution on the aromatic ring preferably involves a radical or radicals selected from the group consisting of $C_1$ to $C_{20}$ branched or straight chain alkyl, $C_1$ to $C_{20}$ cycloalkyl, acetal, ketal, perhaloalkyl, cyclic ether, CN, —CHO, F, Cl, $C_6$ to $C_{20}$ aryl, $—OR^1$, $—CO_2R^1$, $—S(O)R^1$, $—SO_2R^1$, $—SO_3R^1$, and $—C(O)R^1$; where each $R^1$ is independently selected from the group consisting of $C_1$ to $C_{20}$ branched or linear alkyl, $C_1$ to $C_{20}$ cycloalkyl and $C_6$ to $C_{20}$ aryl. In a preferred embodiment, one of the substitutents ortho to the oxygen in the O—Ar group is hydrogen, and the other substituent ortho to the oxygen is selected from the group consisting of $C_1$ to $C_{20}$ branched or linear alkyl, $C_1$ to $C_{20}$ cycloalkyl, acetal, ketal, $C_6$ to $C_{20}$ aryl, cyclic ether, and $OR^1$, where each $R^1$ is independently selected from the group consisting of $C_1$ to $C_{20}$ branched or linear alkyl, $C_1$ to $C_{20}$ cycloalkyl and $C_6$ to $C_{20}$ aryl.

The two aryl groups associated with the phosphorus atom of a diaryloxyphosphonite unit $(—P(—O—Ar)_2)$, or a diarylphosphine unit $(—P(Ar)_2)$, or aryl, aryloxyphosphine unit $(—P(Ar)(—O—Ar))$ may be linked to each other either directly through an aryl carbon to aryl carbon bond or through a linking unit, with the linking unit preferably selected from the group consisting of —O—, —S—, —S(O)—, —S(O)₂—, —C(R²)(R²)—, and N(R²)—; where each R² is independently selected from the group consisting of H, $C_1$ to $C_{20}$ branched or linear alkyl, $C_1$ to $C_{20}$ cycloalkyl, and $C_6$ to $C_{20}$ aryl.

Examples of diarylchlorophosphonite (ClP(Ar)₂), diaryloxychlorophosphonite (ClP(—O—Ar)₂), aryl, aryloxychlorophosphinite (ClP(Ar)(—O—Ar)) phosphorochloridites useful for phosphonylation include, but are not limited to, those shown below:

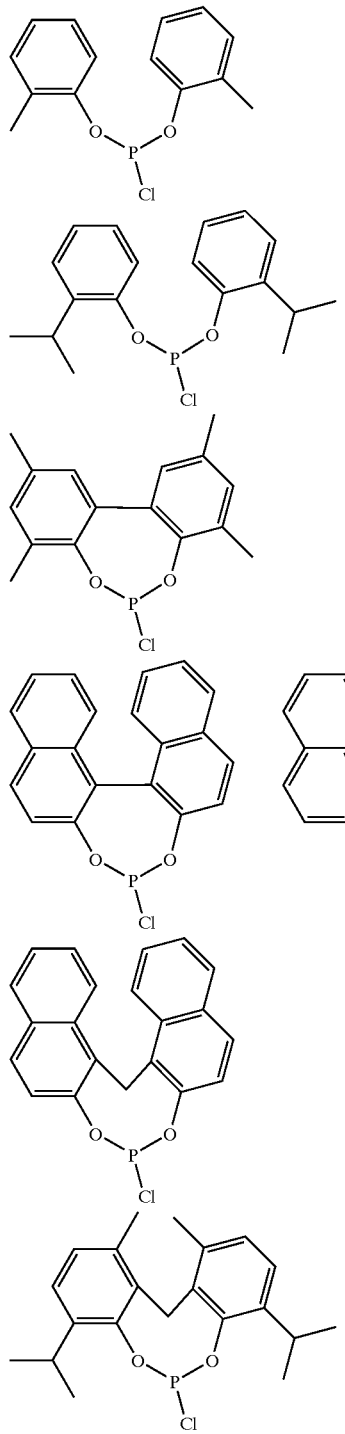

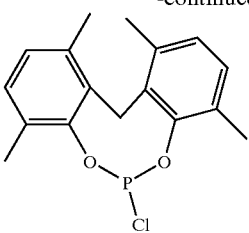

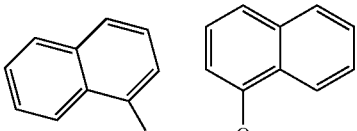

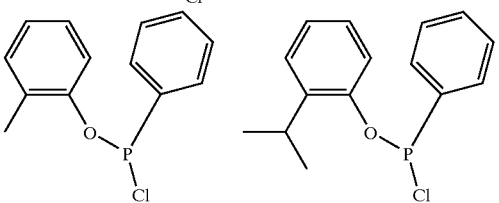

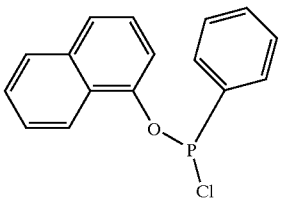

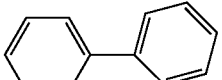

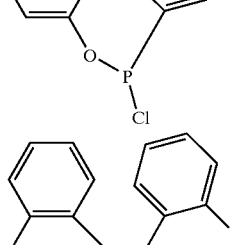

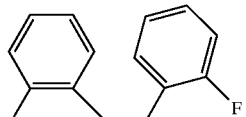

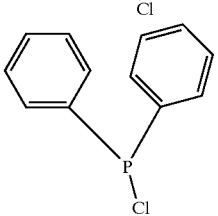

The phosphorochloridite for phosphonylation can be prepared by any means known to one skilled in the art. For example, the phosphorochloridite may be prepared by contacting one molar equivalent of PCl₃ with about two molar equivalents of substituted phenol at a temperature between about −40° C. to 10° C. in the absence of an organic base. The resulting solution is then treated with at least two equivalents of a base, such as an organic base, to produce a phosphorochloridite. When the substituted phenols are replaced with substituted biphenol or substituted alkylidenebisphenol, the phosphorochloridite is similarly prepared by mixing one molar equivalent of PCl₃ with about one molar equivalent of substituted biphenol or substituted alkylidenebisphenol at a temperature between about −40° C. and 10° C. in the absence of an organic base. The resulting solution is then treated with at least two equivalents of an organic base to produce a phosphorochloridite.

When preparing the phosphorochloridite in the above manner, it is important to maintain temperature in the range of −40° C. to 10° C. during the base addition. Since the addition of base results in the formation of an insoluble salt by neutralizing HCl, the reaction mixture can become viscous, making it difficult to achieve good mixing of the base. Good mixing is important to avoid temperature gradients in the reaction mixture which can decrease yield of the desired product. The reaction should be conducted with vigorous stirring or other agitation to allow effective removal of heat from the reaction mixture. Cooling to the required temperature range can be accomplished by techniques well known in the art. The base used in preparing the ligands is generally anhydrous and soluble in the reaction medium. Suitable bases are organic amines. Especially preferred are trialkylamines. The most preferred bases are selected from the group consisting of tributylamine, benzyldimethylamine, triethylamine, diisopropylmethylamine, and combinations of two or more thereof.

The phosphorochloridite can also be prepared by other methods known in the art. For example, one method involves treating phenols with PCl₃, such as described in Polymer, 1992, 33, 161; Inorg. Syn., 1996, 8, 68; U.S. Pat. No. 5,210,260; PCT Pat. App. WO 9622968; and Z. Anorg. Allg. Chem., 1986, 535, 221; incorporated herein by reference. When the phosphorochloridite cannot be prepared in good yield from PCl₃, the preferred method involves the treatment of N,N-dialkyl,diarylphosphoramidite derivatives with HCl. The N,N-dialkyl,diarylphosphoramidite is of the form (R³)₂NP(aryloxy)₂ where R³ is a C₁ to C₄ alkyl group, and can be obtained by reacting phenol or substituted phenol with (R³)₂NPCl₂ by methods known in the art, such as disclosed in WO 9622968, and U.S. Pat. Nos. 5,710,306 and 5,821,378, incorporated herein by reference. The N,N-dialkyl,diarylphosphoramidites can be prepared, for example, as described in Tet. Lett., 1993, 34, 6451; Synthesis, 1988, 2, 142; and Aust. J. Chem., 1991, 44, 233.

For example, the reaction of phosphorus trichloride with one equivalent of substituted phenol will lead to Cl₂P—O—Ar, an aryloxy phosphorodichloridite. The Cl₂P—O—Ar can also be prepared from ((alkyl)₂N)PCl₂ with a substituted phenol followed by treatment with HCl. The reaction of Cl₂P—O—Ar with a divalent bridging group such as a substituted biphenol or substituted binaphthol in the presence of base will lead to a monodentate phosphite. The reaction of Cl₂P—O—Ar with polymers containing hydroxylated biaryls in the presence of base will lead to polymers containing monodentate phosphite moieties. Preferred bases are organic bases such as trialkylamines. The use of mixtures of aryldichlorophosphine and diarylchlorophosphine [Cl₂P(—O—Ar), ClP(—O—Ar)₂, Cl₂P(Ar), ClP(Ar)₂] with polymers containing hydroxylated biaryls will give polymers containing bidentate phosphinite, bidentate phosphite, monodentate phosphinite, and monodentate phosphite groups. Similarly, mixtures containing ClP(Ar) (—O—Ar), ClP(—O—Ar)₂, and ClP(Ar)₂ will lead to polymers containing bidentate phosphonite, bidentate phosphite and bidentate phosphinite groups. Other combinations are possible.

Phosphorochloridite can be prepared from the reaction of phosphorodichloridite with a phenol. An example is the reaction of o-cresol with the phosphorodichloridite of isopropylphenol to give the phosphorochloridite as depicted below.

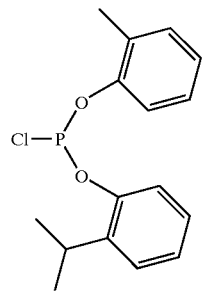

The resultant phosphorochloridite is contacted with an aromatic diol selected from at least one of Formulas III and IV wherein R' is H or M, wherein M is an alkali metal or alkaline earth metal, to prepare a composition comprising at least one compound of Formula I and/or at least one compound of Formula II. The case wherein R' is M is described in U.S. Pat. No. 5,910,600.

An example is shown below:

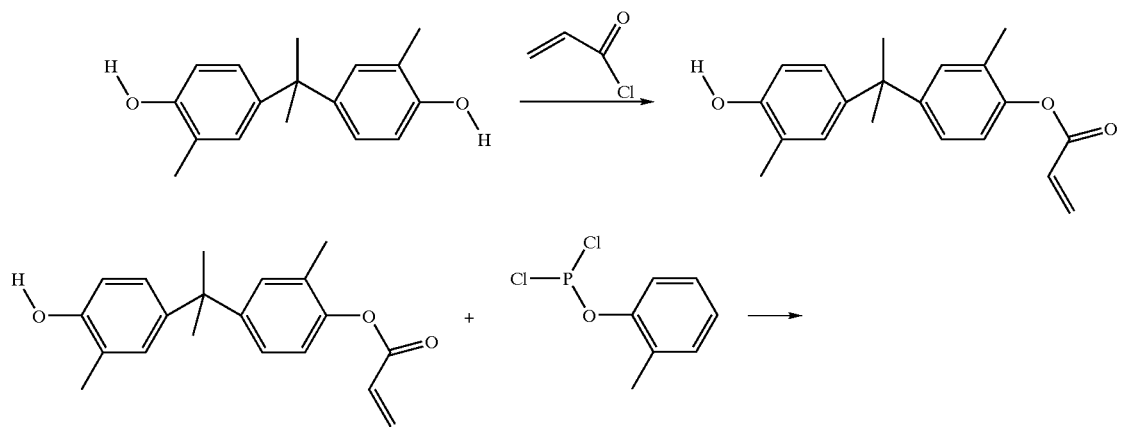

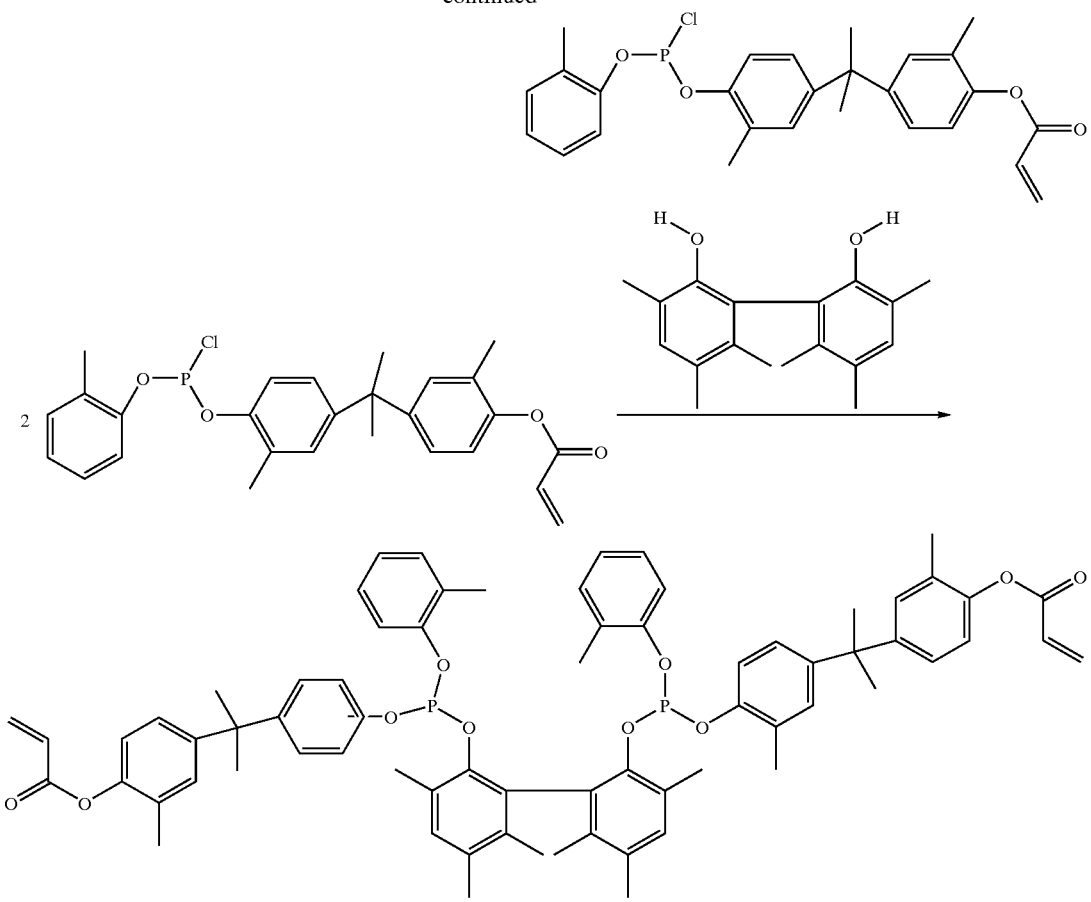

In the third aspect, the present invention provides a method for making a polymeric, phosphorus-containing composition by heating, in the presence of an initiator, preferably a free radical initiator (to effect polymerization), a composition comprising at least one compound of Formula I and/or at least one compound of Formula II, provided at least one R represents ethenyl, propenyl, acryloyl, methacryloyl or the organic radical with a terminal ethenyl, propenyl, acryloyl, or methacryloyl group or at least one R" represents ethenyl, propenyl, or the organic radical with a terminal ethenyl or propenyl group.

Polymerization can be carried out using known methods for polymerization of ethylenic monomers described in the prior art. The polymerization of ethylenic monomers may be initiated with a free radical, carbanion, or carbonium ion. The preferred initiator is a free radical initiator, such as 2,2'-azobisisobutyronitrile (AIBN) or 2,2'-azobis(2-methylpropanenitrile). For example, a composition comprised of vinylic derivative of compounds of Formula I and/or Formula II (1–100 mol %) and one or more different comonomers (e.g., styrene or divinylbenzene) (1–99 mol %) are dissolved in an organic solvent (e.g., toluene or tetrahydrofuran). A free radical initiator (e.g., azobisisobutyronitrile, AIBN) is added. The mixture is held at atmospheric pressure and a temperature of 20° C. to 150° C. for 1 to 100 hours to produce a polymeric composition.

The method of making compounds of Formulas I and/or II generally results in a mixed product containing not only the compounds of Formulas I and/or II, but also other products, including monodentate phosphorus compounds. These compositions may be used as-prepared to produce the polymeric composition. Alternatively, the compounds of Formula I and/or II may be isolated and treated in a purified form. If the composition of Formula I and/or II is used as-prepared to make the polymer, the polymer may contain monodentate phosphites, etc. in addition to compounds of Formula I and/or II.

Compositions comprising the compounds of Formulas I and/or II may also contain comonomers:

(1) not within the scope of the compounds of Formula I and/or II;

(2) selected from the monomers represented by Formulas III and IV; as well as (3) other monomers containing vinyl and acrylate groups.

Some representative comonomers include, but are not limited to: methyl acrylate, bisphenol A dimethacrylate, the diacrylate of 2,2-bis(4-hydroxy-3-methylphenyl)propane, the monoacrylate of 2,2-bis(4-hydroxy-3-methylphenyl) propane, divinylbenzene, 1,1,1-trimethylolpropane trimethacrylate, ethylene glycol dimethylacrylate, pentaerythritol tetraacrylate, hydroquinone diacrylate, benzyl acrylate, methyl methacrylate, styrene, 4-tertbutylstyrene, alpha-methylstyrene, 2,5-dimethylstyrene, and 2-vinylnaphthalene.

In the fifth aspect, the present invention also provides a method to produce a polymeric ligand, which may or may not be identical to that described previously, wherein a composition comprising at least one compound of Formula III and/or at least one compound of Formula IV is heated in the presence of an initiator, followed by phosphonylation of the resultant polymeric precursor to produce a polymeric composition comprising trivalent phosphorus atoms.

The polymeric precursor may be formed by contacting a composition comprising at least one compound of Formula III and/or at least one compound of Formula IV, wherein each R' individually is hydrogen, an alkali metal, an alkaline earth metal or a hydroxyl-protective group selected from alkyl, alkoxyalkyl (e.g., CH₃OCH₂—), carbonylalkyl (e.g., CH₃—C(O)—), and a crown ether formed by linking both R' groups together, with an initiator, preferably a free radical initiator, and heating the resulting mixture to a preselected temperature for a preselected time sufficient to permit reaction, and phosphonylating the resulting polymer.

The term "phosphonylation" means that each hydrogen or protecting group of the hydroxyl groups or protected hydroxyl groups of the respective 2,2'-dihydroxyl-1,1'-binaphthalene or 2,2'-dihydroxyl-1,1'-biphenylene structures is replaced with a trifunctional phosphorus. Typically (after removal of the protective groups by hydrolysis or the like), the hydroxyl groups are reacted with a diaryloxychlorophosphonite (ClP(—O—Ar)₂), a diarylchlorophosphine (ClP(Ar)₂), or an aryl,aryloxychlorophosphinite (ClP(Ar)(—O—Ar)), or mixtures thereof, producing a phosphorus-to-oxygen chemical bond with the elimination of hydrogen chloride or an equivalent. Alternatively, the hydroxyl groups (—OH) can be converted to alkoxides (—OM) wherein M is an alkali metal or alkaline earth metal. Treatment with a diaryloxychlorophosphonite (ClP(—O—Ar)₂), a diarylchlorophosphine (ClP(Ar)₂), or an aryl, aryloxychlorophosphinite (ClP(Ar)(—O—Ar)), or mixtures thereof produces a phosphorus-to-oxygen chemical bond with the elimination of metal chloride (metal being M) or an equivalent.

Compounds of Formulas III and IV containing ethylenic groups (containing a double bond) can be prepared by reaction of the corresponding halide derivative with ethylene under typical Heck-coupling conditions. Typical reaction conditions for Heck-coupling are described in Organic Reactions, 1982, 27, 348; Acc. Chem. Res., 1995, 28, 2; and Pure & Appl. Chem., 1978, 50, 691. For example, 6,6'-dibromo-2,2'-dihydroxy-1,1'-binaphthyl is reacted with Pd(OAc)₂ (5 mol %), P(o-tolyl)₃ (15 mol %) under pressure of ethylene (200 psi) at 75° C., as is shown below.

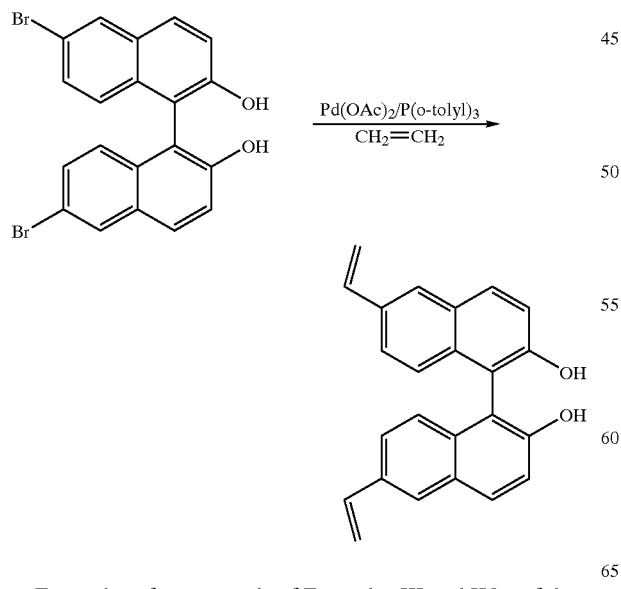

Examples of compounds of Formulas III and IV useful as starting monomer include, but are not limited to, those shown below:

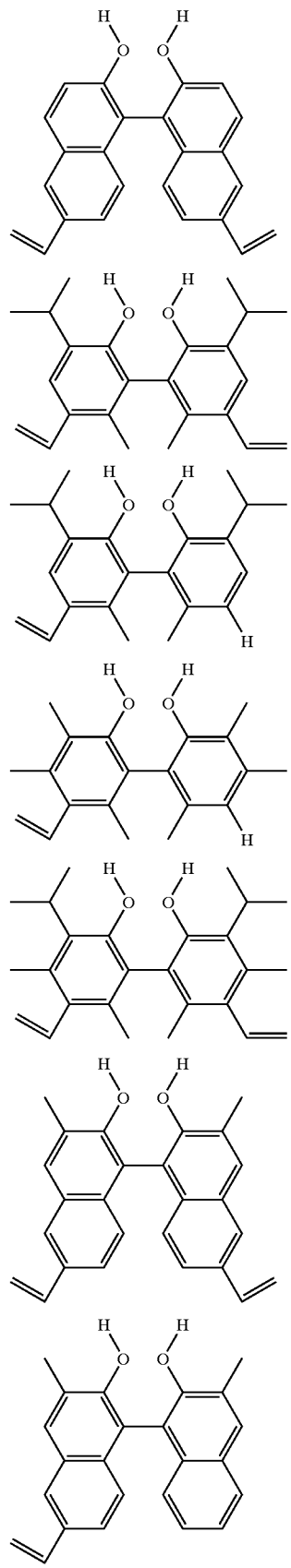

-continued

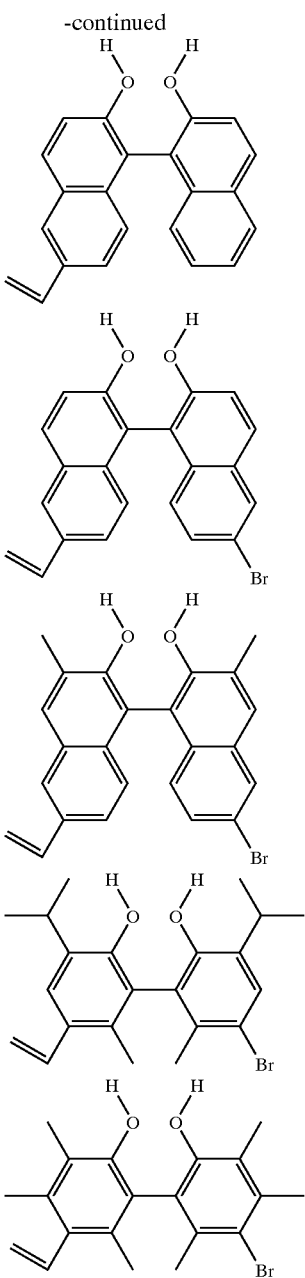

Preferred compounds are those of Formula II, wherein a 2, b=0, R is primary or secondary alkyl located ortho to the oxygen bonded to Ar, wherein y≧1, and wherein at least one R" is primary or secondary alkyl group and is located at the ortho position of the oxygen bonded to the binaphthalene group, or a compound of Formula IV wherein a=2, b=0, R is primary or secondary alkyl located ortho to the oxygen bonded to Ar, wherein x≧1 and wherein at least one R" is primary or secondary alkyl group and is located at the ortho positions of the oxygen bonded to the biphenylene group.

Similar to aspect three, the polymerization of a composition comprising at least one monomer of Formula III and/or at least one monomer of Formula IV can be carried out using known methods for polymerization of ethylenic monomers described in the prior art. The polymerization of ethylenic monomers can be initiated with a free radical, carbanion, or carbonium ion. The preferred initiator is a free radical initiator, specifically 2,2'-azobisisobutyronitrile (AIBN) or 2,2'-azobis(2-methylpropanenitrile). For example, the mixture could be heated in the presence of a free radical initiator at atmospheric pressure and a temperature of 20° C. to 150° C. for 1 to 100 hours to produce a polymeric composition.

The polymerization may be carried out in the presence of comonomers, which can be selected from the monomers represented by Formulas I and II, as well as other monomers containing vinyl and acrylate groups. Some representative comonomers include, but are not limited to: methyl acrylate, bisphenol A dimethacrylate, the diacrylate of 2,2-bis(4-hydroxy-3-methylphenyl)propane, the monoacrylate of 2,2-bis(4-hydroxy-3-methylphenyl)propane, divinylbenzene, styrene, 1,1,1-trimethylolpropane trimethacrylate, ethylene glycol dimethylacrylate, pentaerythritol tetraacrylate, hydroquinone diacrylate, benzyl acrylate, and methyl methacrylate.

As used herein, the structures used in Formulas I, II, III, and IV, and the expressions "2,2'-dihydroxyl-1,1'-binaphthalene" and "2,2'-dihydroxyl-1,1'-biphenylene" denote not only the diol structure, but also the corresponding so-called protected diol structures wherein the hydrogen of the hydroxyl group is temporarily replaced by various organic radicals as generally known in the art. Therefore, the polymerization and/or copolymerization of the vinyl- or acrylate-substituted 2,2'-dihydroxyl-1,1'-binaphthalene or 2,2'-dihydroxyl-1,1'-biphenylene (or mixtures thereof), can, in principle, be performed either in the diol or the protected diol form. In the protected form of Formulas III and IV, protecting groups are provided on any naphtholic or phenolic hydroxyl groups prior to polymerization and then preferably removed prior to phosphonylation. Suitable protecting groups include ethers, alkyls, esters, and crown ethers. Other protecting groups as generally known to those skilled in the art of protecting hydroxyl moieties during reactions are suitable for this purpose.

In its seventh aspect, the present invention further provides a method to produce a polymeric, phosphorus-containing composition by heating a phosphorochloridite containing at least one acrylate or methyl acrylate group in the presence of an initiator, preferably a free radical initiator, to produce a polymer containing phosphorochloridite, and further reacting this polymer with a composition comprising at least one compound of Formula III and/or Formula IV wherein each R' individually is H or M, with the provision that if R' is protected, the protecting group must be removed before reacting the compound of Formula III and/or Formula IV with the polymer containing phosphorochloridite.

Preferred compounds are when the trivalent phosphorus is a diaryloxyphosphite unit, —P(—O—Ar)$_2$, and a compound of Formula III, wherein a=2, b=0, the Ar group contains a primary or secondary alkyl located ortho to the oxygen bonded to Ar, wherein y≧1 and wherein at least one R" is primary or secondary alkyl group and is located at the ortho position of the oxygen bonded to the binaphthalene group, or a compound of Formula IV wherein a=2, b=0, the Ar group contains a primary or secondary alkyl located ortho to the oxygen bonded to Ar, wherein x 1 and wherein at least one R" is primary or secondary alkyl group and is located at the ortho positions of the oxygen bonded to the biphenylene group.

The phosphorochloridite for use in the seventh aspect may be prepared as described above. Heating the phosphorochloridite in the presence of an initiator provides a polymeric phosphorochloridite. Contacting the polymeric phosphorochloridite with the composition comprising at least one compound of Formula III and/or Formula IV provides the polymeric, phosphorus-containing composition.

The above processes describe the synthesis of polymeric, phosphorus-containing ligands of various structures. It is known in the art that the solubility properties of polymers are affected by their structure. It is preferred that the polymeric ligands of this invention be as insoluble as possible, consistent with retaining substantial catalytic activity. If the resulting polymers are insoluble, they can be separated by filtration from the reaction mixtures in which they are used and then recycled. If the polymeric ligands are partially soluble in the reaction mixture, they can be separated by filtration of the insoluble ligand and then precipitation of the soluble ligand with a solvent in which the ligand has extremely low solubility or by precipitation of the soluble ligand and filtration of the reaction mixture. If the ligands are completely soluble in the reaction mixture, they can be separated by precipitation with a solvent in which the ligand has extremely low solubility.

Use of the Present Phosphorus-containing Ligands in Catalyst Compositions

In the ninth aspect, the present invention provides a catalyst composition, optionally containing a Lewis Acid, comprising at least one monomeric ligand composition of Formulas I and/or II combined with at least one Group VIII transition metal, transition metal compound, and/or transition metal complex, or at least one polymeric ligand composition of the present invention combined with at least one Group VIII transition metal, transition metal compound, or transition metal complex, and/or the catalyst material of aspect three of the present invention wherein the polymerization is carried out in the presence of at least one Group VIII transition metal, transition metal compound, or transition metal complex. Generally, any Group VIII metal or metal compound can be used to combine with the composition. The term "Group VIII" refers to the ACS version of the Periodic Table of the Elements, "CRC Handbook of Chemistry and Physics", 67$^{th}$ edition, Boca Raton, Fla.: CRC Press, 1986–1987.

Generally, a Group VIII metal or compound thereof is combined with at least one monomeric or polymeric ligand of the present invention to provide the catalyst. Among the Group VIII metal compounds, nickel, cobalt, and palladium compounds are preferred for hydrocyanation catalysts. A nickel compound is most preferred. A zero-valent nickel compound that contains a ligand that can be displaced by the polymeric ligand of the present invention is the most preferred source of Group VIII metal or Group VIII metal compound. Zero-valent nickel compounds can be prepared or generated according to methods known in the art, such as those described in U.S. Pat. Nos. 3,496,217; 3,631,191; 3,846,461; 3,847,959; and 3,903,120; incorporated herein by reference. Three preferred zero-valent nickel compounds are $Ni(COD)_2$ (COD is 1,5-cyclooctadiene), $Ni\{P(O\text{-}o\text{-}C_6H_4CH_3)_3\}_3$ and $Ni\{P(O\text{-}o\text{-}C_6H_4CH_3)_3\}_2(C_2H_4)$, as known in the art.

Alternatively, divalent nickel compounds can be combined with a reducing agent to serve as a source of zero-valent nickel in the reaction. Suitable divalent nickel compounds include compounds of the formula $NiZ^2_2$ where $Z^2$ is halide, carboxylate, or acetylacetonate. Suitable reducing agents include metal borohydrides, metal aluminum hydrides, metal alkyls, Li, Na, K, or $H_2$. Elemental nickel, preferably nickel powder, when combined with a halogenated catalyst, as described in U.S. Pat. No. 3,903,120 (incorporated herein by reference) is also a suitable source of zero-valent nickel.

The chelating arrangement of donor atoms in bidentate ligands results in a strong ligand-metal interaction and thus greatly minimizes the potential for metal leaching. It is possible to alter the spacing between the chelating atoms, the steric environment of these atoms, and the electronic properties of the donor atoms, offering control of ligand coordination properties, thereby optimizing catalyst performance.

Hydrocyanation Using the Present Phosphorus-containing Ligands

In the tenth aspect of the present invention, the monomers of Formulas I and/or II and/or the polymeric ligand compositions of the present invention may be used to form catalysts (with or without a Lewis Acid) which may be used for the hydrocyanation of organic compounds. The process comprises contacting, in the presence of the catalyst, an unsaturated organic compound with a hydrogen cyanide-containing fluid under conditions sufficient to produce a nitrile, wherein the catalyst comprises a Group VIII metal, at least one of the present ligands described above, and optionally a Lewis acid. The term "fluid" may refer to a gas, liquid, or mixture thereof. Any fluid containing about 1 to 100% HCN can be used. Pure hydrogen cyanide may be used. Preferably, the HCN contains less than 40 ppm sulfuric acid, less than 20 ppm sulfur dioxide, less than 20 ppm cyanogen, less than 10 ppm epoxide, less than 10 ppm carbon monoxide, less than 20 ppm acrylonitrile, and less than 100 ppm peroxides.

The hydrocyanation process can be carried out, for example, by charging a suitable vessel such as a reactor with an unsaturated compound, catalyst composition, and solvent, if any, to form a reaction mixture. Hydrogen cyanide can be initially combined with other components to form the mixture. However, it is preferred that HCN be added slowly to the mixture after the other components have been combined. Hydrogen cyanide can be delivered as a liquid or as a vapor to the reaction. As an alternative, a cyanohydrin can be used as the source of HCN, as described in, for example, U.S. Pat. No. 3,655,723, incorporated herein by reference. Preferably, the unsaturated compound contains less than 100 ppm peroxides.

Another suitable technique is to charge the vessel with the catalyst and the solvent (if any) to be used, and feed both the unsaturated compound and the HCN slowly to the reaction mixture.

The molar ratio of unsaturated compound to catalyst can be varied from about 10:1 to about 100,000:1. The molar ratio of HCN to catalyst generally is varied from about 10:1 to 100,000:1, preferably 100:1 to 2,500:1, for a batch operation. In a continuous operation, such as when using a fixed bed catalyst type of operation, a higher proportion of catalyst can be used, such as 5:1 to 100,000:1, preferably 100:1 to 5,000:1, HCN to catalyst.

Preferably the reaction mixture is agitated, for example by stirring or shaking. The reaction product can be recovered by conventional techniques such as distillation. The reaction can be run either batchwise or continuously.

The hydrocyanation can be carried out with or without a solvent. The solvent, if used, can be liquid at the reaction temperature and pressure and inert towards the unsaturated compound and the catalyst. Suitable solvents include hydrocarbons such as benzene, xylene, or combinations thereof; ethers, such as tetrahydrofuran (THF); nitrites, such as acetonitrile, benzonitrile, adiponitrile, or combinations of two or more thereof. The unsaturated compound to be hydrocyanated can itself serve as the solvent. Hydrocyanation can also be carried out in the gas phase.

The exact temperature is dependent to a certain extent on the particular catalyst being used, the particular unsaturated compound being used and the desired reaction rate. Normally, temperatures of from −25° C. to 200° C. can be used, the range of 0° C. to 150° C. being preferred.

Atmospheric pressure is satisfactory for carrying out the reaction, and hence pressures of from about 0.05 to 10 atmospheres (50.6 to 1013 kPa) are preferred. Higher pressures, up to 10,000 kPa or more, can be used, if desired, but any benefit that may be obtained thereby would need to justify the increased cost of such operations.

The time required can be in the range of a few seconds to many hours (such as 2 seconds to 24 hours), depending on the particular conditions and method of operation.

The unsaturated compound can have 2 to about 30 carbon atoms per molecule. It can have the formula of $R^4CH=CH—CH=CR^5$, $CH=CH—(CH_2)_q—R^6$, $CH_3—(CH_2)_n—CH=CH—(CH_2)_q—R^6$, and combinations of two or more thereof in which $R^4$ and $R^5$ are each independently H, $C_1$ to $C_3$ alkyl, or combinations thereof; $R^6$ is H, CN, $CO_2R^7$, perfluoroalkyl having 1 to about 20 carbon atoms; n is an integer of 0 to 12; q is an integer of 0 to 12 when $R^6$ is H, $CO_2R^7$ or perfluoroalkyl; q is an integer of 1 to 12 wherein $R^6$ is CN; and $R^7$ is $C_1$ to $C_{12}$ alkyl or cycloalkyl, $C_6$ to $C_{20}$ aryl, or combinations thereof.

The unsaturated compound can be an acyclic, aliphatic, monoethylenically unsaturated compound or cyclic unsaturated compound, or combinations thereof. Non-limiting examples of ethylenically unsaturated compounds are shown in Formulas V and VII, and the corresponding terminal nitrile compounds produced are illustrated by Formulas VI and VIII, respectively, wherein $R^6$ is the same as disclosed above.

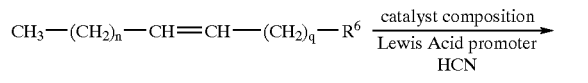

Formula V

Formula VI

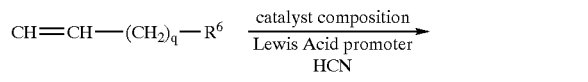

Formula VII

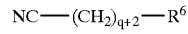

Formula VIII

The hydrocyanation reaction yields internal as well as terminal nitriles. Preferred products are terminal nitriles. Starting compounds of Formula V yield terminal nitriles of Formula VI, while those of Formula VII yield terminal nitriles of Formula VIII.

Suitable unsaturated compounds include, but are not limited to, ethylenically unsaturated organic compounds containing from 2 to about 30 carbon atoms. Examples of suitable ethylenically unsaturated compounds are ethylene, cyclohexene, propylene, 1-butene, 2-pentene, 2-hexene, and combinations of two or more thereof. The unsaturated compound may also be diethylenically unsaturated such as allene. Other suitable substituted, ethylenically unsaturated compounds are 3-pentenenitrile, 4-pentenenitrile, methyl 3-pentenoate, combinations of two or more thereof, and ethylenically unsaturated compounds having perfluoroalkyl substituents such as, for example, $C_bF_{2b+1}$, where b is an integer of up to 20. The monoethylenically unsaturated compounds can also be conjugated to an ester group such as methyl 2-pentenoate. Preferred unsaturated compounds are linear alkenes, linear alkenenitriles, linear alkenoates, linear alkyl 2-alkenoates, perfluoroalkyl ethylenes, and combinations of two or more thereof. Most preferred substrates include 3- and 4-pentenenitrile, alkyl 2-, 3-, and 4-pentenoates, and $C_bF_{2b+1}CH=CH_2$ (where b is 1 to 12), and combinations of two or more thereof. 3-Pentenenitrile and 4-pentenenitrile are especially preferred olefins. Preferably, the pentenenitriles contain less than 100 ppm peroxides.

When non-conjugated, acyclic, aliphatic, monoethylenically unsaturated compounds are used, up to about 10% by weight of the monoethylenically unsaturated compound can be present in the form of a conjugated isomer, which itself may undergo hydrocyanation. For example, when 3-pentenenitrile is used, as much as 10% by weight thereof may be 2-pentenenitrile (as used herein, the term "pentenenitrile" is intended to be identical with "cyanobutene"). Suitable unsaturated compounds include unsubstituted hydrocarbons, as well as hydrocarbons substituted with groups that do not attack the catalyst, such as the cyano group.

The preferred products are terminal alkane nitriles, linear dicyanoalkylenes, linear aliphatic cyanoesters, 3-(perfluoroalkyl)propionitrile, and combinations of two or more thereof. Most preferred products are adiponitrile, alkyl 5-cyanovalerate, $C_bF_{2b+1}CH_2CH_2CN$, where b is 1 to 12, and combinations of two or more thereof.

The process of this invention can be carried out in the presence of one or more Lewis acid promoters that affect both the activity and the selectivity of the catalyst system. The promoter may be an inorganic or organometallic compound in which the cation is selected from scandium, titanium, vanadium, chromium, manganese, iron, cobalt, copper, zinc, boron, aluminum, yttrium, zirconium, niobium, molybdenum, cadmium, rhenium, lanthanum, europium, ytterbium, tantalum, samarium, and tin. Examples include $ZnBr_2$, $ZnI_2$, $ZnCl_2$, $ZnSO_4$, $CuCl_2$, CuCl, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_2$, $ClTi(OiPr)_3$, $MnCl_2$, $ScCl_3$, $AlCl_3$, $(C_8H_{17})AlCl_2$, $(C_8H_{17})_2AlCl$, $(iso-C_4H_9)_2AlCl$, $Ph_2AlCl$, $PhAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $(C_6H_5)_3SnX$, where X=$CF_3SO_3$, $CH_3C_6H_5SO_3$, or $(C_6H_5)_3BCN$ and $TaCl_5$. Suitable promoters are further described in U.S. Pat. Nos. 3,496,217; 3,496,218; and 4,774,353; the disclosures of which are incorporated herein by reference. These include metal salts (such as $ZnCl_2$, $CoI_2$, and $SnCl_2$), and organometallic compounds (such as $R^8AlCl_2$, $R^8SnO_3SCF_3$, and $R^8B$, where $R^8$ is an alkyl or aryl group). U.S. Pat. No. 4,874,884 (incorporated herein by reference) describes how synergistic combinations of promoters can be chosen to increase the catalytic activity of the catalyst system. Preferred promoters include $CdCl_2$, $FeCl_2$, $ZnCl_2$, $B(C_6H_5)_3$, and $(C_6H_5)_3Sn(CF_3SO_3)$, $CH_3C_6H_5SO_3$, or $(C_6H_5)_3BCN$. The mole ratio of promoter to Group VIII transition metal present in the reaction can be within the range of about 1:16 to about 50:1.

Hydrocyanation can also be carried out with a conjugated olefin. With conjugated olefins, a Lewis acid promoter is optional. Examples of conjugated olefins containing from about 4 to about 15, preferably 4 to 10 carbon atoms are 1,3-butadiene, cis and trans-2,4-hexadienes, cis and trans-1,3-pentadienes, and combinations of two or more thereof. Butadiene is especially preferred by reason of its commercial importance in the production of adiponitrile. Preferably, the butadiene contains less than 20 ppm t-butyl catechol, less than 500 ppm vinylcyclohexene, and less than 100 ppm peroxides.

The following Formulas IX and X illustrate some suitable starting conjugated olefins, wherein each one of $R^9$ and $R^{10}$, independently, is H or a $C_1$ to $C_3$ alkyl group.

$CH_2=CH—CH=CH_2$  $R^9CH=CH—CH=CHR^{10}$ 1,3-butadiene

IX                X

Formulas XI, XII, and XIII represent the products obtained from 1,3-butadiene and HCN wherein 3PN denotes 3-pentenenitrile, 4PN is 4-pentenenitrile, and 2M3BN is 2-methyl-3-butenenitrile.

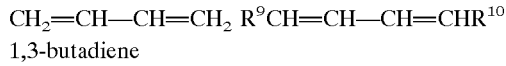

XI

2M3BN

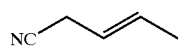

XII

3PN

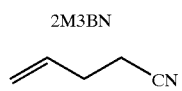

XIII

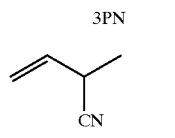

4PN

The reaction of a conjugated olefin and a HCN-containing fluid can be carried out in the same manner as that described above in relation to monoethylenically unsaturated compounds.

Isomerization Using the Present Phosphorus-containing Ligands

In the eleventh aspect of the present invention, the monomers of Formulas I and/or II and/or the ligand compositions of the present invention may be used to form catalysts, which may be used for the isomerization of branched nitriles to linear nitriles. The isomerization comprises contacting an alkenyl nitrile with a catalyst disclosed above, under conditions sufficient to isomerize the alkenyl nitrile. The process can be run with or without a Lewis acid. Examples of suitable alkenyl nitriles include, but are not limited to, 2-alkyl-3-monoalkenenitriles, 3-alkenenitriles, or combinations thereof. The isomerization can be carried out under substantially similar conditions as described above in relation to hydrocyanation. Preferably, the branched nitrile contains less than 100 ppm peroxides.

The 2-alkyl-3-monoalkenenitrile used as the starting material in the isomerization can be made by the hydrocyanation of a diolefin as described above, or can come from any other available sources. The olefinic double bond in the 2-alkyl-3-monoalkenenitriles used as starting materials in the isomerization cannot be conjugated to the triple bond of the cyano group. Suitable starting 2-alkyl-3-monoalkenenitriles can also carry groups that do not attack the catalyst, for example, another cyano group. Preferably, the starting 2-alkyl-3-monoalkenenitriles contain from 5 to 8 carbon atoms, excluding any additional substitution. 2-Methyl-3-butenenitrile is an especially important starting material, because it is used to produce adiponitrile. Other representative nitrile starting materials include 2-ethyl-3-butenenitrile and 2-propyl-3-butenenitrile.

When the starting nitrile is 2-methyl-3-butenenitrile (2M3BN, Formula XIII above), the isomerization products are 3PN and 4PN, as shown in Formulas XI and XII, above.

The isomerization process of this invention can be carried out, for example, at atmospheric pressure and at any temperature in the range of 10–200° C., preferably in the range of 60–150° C. The pressure is not critical, however, and can be above or below atmospheric pressure, if desired. Any of the conventional batch or continuous flow procedures may be used either in the liquid phase or in the vapor phase (with respect to the relatively volatile 2-methyl-3-butenenitrile reactant and linear pentenenitrile products). The reactor may be of any mechanically and chemically resistant material, and is usually of glass or an inert metal or alloy, such as nickel, copper, silver, gold, platinum, stainless steel, Monel® metal alloy or Hastelloy® metal alloy.

The process can be carried out in the absence or in the presence of a solvent or diluent. Any solvent or diluent that is inert to, or nondestructive of, the catalyst can be used. Suitable solvents include, but are not limited to, aliphatic or aromatic hydrocarbons (hexane, cyclohexane, benzene), ethers (diethyl ether, tetrahydrofuran, dioxane, glycol dimethyl ether, anisole), esters (ethyl acetate, methyl benzoate), nitriles (acetonitrile, benzonitrile), or combinations of two or more thereof.

The catalyst (complex of Group VIII metal, preferably nickel, and ligand) is essentially nonvolatile, whereas the 2-methyl-3-butenenitrile reactant and the linear pentenenitrile products are relatively volatile.

Accordingly, in a continuous flow procedure, the catalyst can be a component of the flowing system in a slurry-liquid-phase operation. It can also be in a mobile non-flowing liquid state in a semi-vapor phase operation, or it may be in a fixed-bed state in a conventional flowing vapor-phase operation or flowing liquid-phase operation.

The time required for the isomerization process to obtain a practical level of conversion of, for example, 2-alkyl-3-monoalkenenitrile, to linear alkenenitrile is dependent upon the temperature of reaction, i.e., operation at lower temperature generally requires a longer time than operation at a higher temperature. A practical reaction time can be in the range of a few seconds to many hours (2 seconds to about 24 hours), depending on the particular conditions and method of operation.

The molar ratio of 2-alkyl-3-monoalkenenitrile to catalyst is generally greater than 1:1, usually in the range from about 5:1 to 20,000:1, preferably 100:1 to 5,000:1, for a batch or continuous operation.

Hydroformylation Using the Present Phosphorus-containing Ligands

In the twelfth aspect of the present invention, the monomers of Formulas I and/or II and/or the ligands of the present invention may be used to form catalysts that may be used for hydroformylation of unsaturated organic compounds with 2 to 20 carbon atoms or cyclic unsaturated compound to produce corresponding aldehydes. The catalyst comprises a Group VIII metal or Group VIII metal compound combined with at least one ligand of the present invention. Preferred Group VIII metals for hydroformylation reactions are rhodium, iridium, and platinum, the most preferred being rhodium. The Group VIII metal may be in the form of a compound, such as a hydride, halide, organic acid salt, ketonate, inorganic acid salt, oxide, carbonyl compound, amine compound, or combinations of two or more thereof. Preferred Group VIII metal compounds are Ir$_4$(CO)$_{12}$, IrSO$_4$, RhCl$_3$, Rh(NO$_3$)$_3$, Rh(OAc)$_3$, Rh$_2$O$_3$, Rh(acac)(CO)$_2$, [Rh(OAc)(COD)]$_2$, Rh$_4$(CO)$_{12}$, Rh$_6$(CO)$_{16}$, RhH(CO)(Ph$_3$P)$_3$, [Rh(OAc)(CO)$_2$]$_2$, [RhCl(COD)]$_2$, and combinations of two or more thereof ("acac" is an acetylacetonate group; "OAc" is an acetyl group; "COD" is 1,5-cyclooctadiene; and "Ph" is a phenyl group). However, it should be noted that the Group VIII metal compounds are not necessarily limited to the above listed compounds. Rhodium compounds suitable for hydroformylation can be prepared or generated according to techniques well known in the art, as described, for example, in PCT Pat. App. WO9530680; U.S. Pat. No. 3,907,847; and J. Am. Chem. Soc., 1993, 115, 2066, incorporated herein by reference. Rhodium compounds that contain ligands which can be displaced by the present phosphite ligands are a preferred source of rhodium. Examples of such preferred rhodium compounds are Rh(CO)$_2$(acac), Rh(CO)$_2$(C$_4$H$_9$COCHCO-t-C$_4$H$_9$), Rh$_2$O$_3$, Rh$_4$(CO)$_{12}$, Rh$_6$(CO)$_{16}$, Rh(O$_2$CCH$_3$)$_2$, Rh(2-ethylhexanoate), and combinations of two or more thereof.

The amount of transition metal in the catalyst may be varied and may be determined by balancing catalyst activity and process economy. In general, the molar ratio of ligand to transition metal generally can be from about 1:1 to about 100:1, preferably from about 2:1 to about 20:1 moles phosphorus per mole metal.

The reactant of the hydroformylation process is an unsaturated organic compound having at least one "C=C" bond in the molecule and preferably 2 to about 20 carbon atoms. Examples of suitable ethylenically unsaturated organic compounds include, but are not limited to, linear terminal olefinic hydrocarbons (i.e., ethylene, propylene, 1-butene, 1-pentene, 1-hexene, 1-octene, 1-nonene, 1-decene, 1-tetradecene, 1-hexadecene, 1-octadecene, 1-eicosene and 1-dodecene); cyclic olefinic hydrocarbons (i.e., cyclohexene, cyclopentene); branched terminal olefinic hydrocarbons (i.e., isobutene and 2-methyl-1-butene); linear internal olefinic hydrocarbons (i.e., cis- and trans-2-butene, cis- and trans-2-hexene, cis- and trans-2-octene, and cis- and trans-3-octene); branched internal olefinic hydrocarbons (i.e., 2,3-dimethyl-2-butene, 2-methyl-2-butene and 2-methyl-2-pentene); terminal olefinic hydrocarbons; internal olefinic hydrocarbon mixtures (i.e., octenes, prepared by dimerization of butenes); cyclic olefins (i.e., cyclohexene, and cyclooctene); and combinations of two or more thereof.

Examples of suitable unsaturated compounds also include those substituted with an unsaturated hydrocarbon group, including olefinic compounds containing an aromatic substituent such as styrene, alpha-methylstyrene and allylbenzene.

The unsaturated organic compound can also be substituted with one or more functional groups containing a heteroatom, such as oxygen, sulfur, nitrogen or phosphorus. Examples of these heteroatom-substituted, ethylenically unsaturated, organic compounds include vinyl methyl ether, methyl oleate, oleyl alcohol, 3-pentenenitrile, 4-pentenenitrile, 3-pentenoic acid, 4-pentenoic acid, methyl 3-pentenoate, 7-octen-1-al, acrylonitrile, acrylic acid esters, methyl acrylate, methacrylic acid esters, methyl methacrylate, acrolein, allyl alcohol, 3-pentenal, 4-pentenal, and combinations of two or more thereof.

The hydroformylation process of the invention can be illustrated as follows:

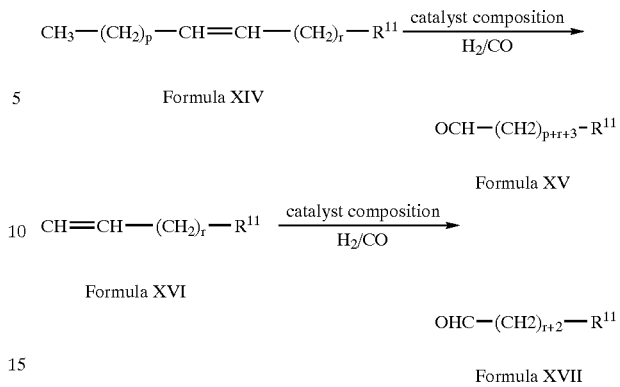

Formula XIV

Formula XV

Formula XVI

Formula XVII

In the above equations, $R^{11}$ is H, —CN, —CO$_2$R$^{12}$, —C(O)NR$^{12}$R$^{12}$, —CHO, —OR$^{12}$, OH, or combinations of two or more thereof; p is an integer from 0 to 12; and r is an integer from 0 to 12. Each $R^{12}$ is independently selected from the group consisting of H, C$_1$ to C$_{20}$ branched or straight chain alkyl, C$_1$ to C$_{20}$ cycloalkyl, and C$_6$ to C$_{20}$ aryl.

Particularly preferred unsaturated organic compounds are 3-pentenenitrile, 3-pentenoic acid, 3-pentenal, allyl alcohol, and alkyl 3-pentenoate, such as methyl 3-pentenoate, and combinations of two or more thereof, preferably the 3-pentenenitrile, 3-pentenoic acid, 3-pentenal, allyl alcohol, and alkyl 3-pentenoate, such as methyl 3-pentenoate, and combinations of two or more thereof. Impurities that are detrimental to the catalyst should be kept to a minimum. Preferably, the unsaturated organic compounds contain less than 100 ppm peroxides. The linear aldehyde compound prepared by the present process starting with one of these compounds can be used advantageously in the preparation of ε-caprolactam, hexamethylenediamine, 6-aminocaproic acid, 6-aminocapronitrile or adipic acid, which are precursors for nylon-6 and/or nylon-6,6.

The hydroformylation process of the invention also can be carried out with a mixture that comprises two or more unsaturated organic compounds. For example, 3-pentenenitrile can be present in a mixture containing 4-pentenenitrile. Because the 4-isomer reacts in a similar fashion as the corresponding 3-isomer to the desired linear aldehyde, a mixture of isomers can be used directly in the present process.

The 3-pentenenitrile may be present in mixtures containing impurities that do not interfere with the hydroformylation reaction. An example of such an impurity is 2-pentenenitrile.

The hydroformylation process of the invention can be carried out by any means known to one skilled in the art, such as, for example, the one disclosed in U.S. Pat. No. 4,769,498, the disclosure of which is incorporated herein by reference. Generally, the process can be carried out under any condition sufficient to effect the production of a desired aldehyde. For example, the temperature can be from about 0° C. to 200° C., preferably from about 50 to 150° C., and more preferably from 85° to 110° C. The pressure may vary from atmospheric pressure to 5 MPa, preferably from 0.1 to 2 MPa. The pressure is, as a rule, equal to the combined hydrogen and carbon monoxide partial pressures. Inert gases also may be present; the pressure may vary from atmospheric pressure to 15 MPa when inert gases are present. The molar ratio of hydrogen to carbon monoxide is generally between 10:1 and 1:10, and preferably between 6:1 and 1:2 moles hydrogen/mole carbon monoxide. It is most preferred that a 1:1 ratio of carbon monoxide and hydrogen is used.

The amount of catalyst is selected so that favorable results can be obtained with respect to catalyst activity and process economy. In general, the amount of transition metal in the reaction medium, which comprises an unsaturated organic compound, a catalyst composition, and solvent (if present), can be between 10 and 10,000 ppm and more preferably between 50 and 1,000 ppm, calculated as free metal.

The solvent may be the mixture of reactants of the hydroformylation reaction itself, such as the starting unsaturated compound, the aldehyde product and/or by-products. Other suitable solvents include saturated hydrocarbons (i.e., kerosene, mineral oil, or cyclohexane), ethers (i.e., diphenyl ether or tetrahydrofuran), ketones (i.e., acetone, cyclohexanone), nitriles (i.e., acetonitrile, adiponitrile or benzonitrile), aromatics (i.e., toluene, benzene, or xylene), esters (i.e., methyl valerate, caprolactone), dimethylformamide, or combinations of two or more thereof.

The hydroformylation process can be run in solution or in the gas phase. When the hydroformylation is carried out in the vapor phase, the preferred temperature range is from about 50° C. to about 180° C., most preferably from about 90° C. to 110° C. The temperature must be chosen high enough so as to maintain all of the reactants and products in the vapor phase, but low enough to prevent deterioration of the catalyst. The particular preferred temperature depends to some extent on the catalyst being used, the olefinic compound being used, and the desired reaction rate. The operating pressure is not particularly critical and can be from about 0.1 to 1.0 MPa. The pressure and temperature combination must be chosen so as to maintain reactants and products in the vapor phase. A given catalyst is loaded into a reactor, such as a tubular reactor, taking care to avoid exposure of oxygen-sensitive catalysts to oxygen from the air. A gaseous mixture of the desired olefinic compound, carbon monoxide and hydrogen, along with any desired diluent, such as nitrogen, helium or argon, is then passed through the reactor while contacting the catalyst. The reaction products are generally liquid at room temperature and are conveniently recovered by cooling. The reactor effluent can be directly connected to a sampling valve and can be analyzed by gas chromatography. Aldehydic products, such as linear and branched butyraldehydes obtained from hydroformylation of propylene, can be quantitatively separated and analyzed using a 30M DB-Wax® capillary GC column.

For the hydrocyanation, isomerization, and hydroformylation processes described herein, a non-oxidizing environment is desirable in order to retard oxidative deactivation of the catalyst. Accordingly, an inert atmosphere, e.g., nitrogen, is preferably used, although air can be used, if desired, at the expense of loss of a proportion of the catalyst acitivity through oxidation. Impurities that are detrimental to the catalyst should be kept to a minimum.

The following examples are presented to further illustrate specific features and embodiments of the present invention including various methods of preparing the polymeric substrate on which the phosphorus-containing ligand is to be formed and methods of forming the phosphorus-containing ligand compositions. The following examples are not intended to be limiting. Similarly the specific reactions and compounds when identified structurally by chemical formula are intended to be illustrative of the reaction pathway for the formation of the present phosphorus-containing bidentate ligand compositions. It should be appreciated that other species and distribution of products will be present, as generally known in the art, and that any performance data associated with such compositions was derived using the mixture as-produced, without isolation or separation of the specific compounds, unless otherwise indicated. All parts, proportions, and percentages are by weight, unless otherwise indicated.

In the examples, 3PN stands for 3-pentenenitrile, ADN stands for adiponitrile, COD stands for 1,5-cyclooctadiene, THF stands for tetrahydrofuran, Vazo®64 free radical initiator represents 2,2'-azobis(2-methylpropanenitirile) from E.I. Du Pont de Nemours & Co., Inc.; AIBN stands for 2,2'-azobisisobutyronitrile, DVB stands for divinylbenzene and oTTP stands for tris(o-tolyl) phosphite.

In evaluating the performance of the respective phosphorus-containing ligand compositions, the following general procedures were employed unless otherwise noted:

Preparation of Catalyst for Hydrocyanation Reactions

Method A A catalyst solution is prepared by adding 0.0039 grams of $Ni(COD)_2$ (0.014 mmol) dissolved in 0.320 mL toluene to a specified quantity of the respective phosphorus-containing polymeric ligand composition being evaluated dissolved in 0.200 mL toluene.

Method B The specified weight of Ni containing solid in a reaction vial fitted with a septum cap is used as prepared for butadiene hydrocyanation and for 2-methyl-3-butenenitrile (2M3BN) isomerization and contacted with 0.125 mL of THF for 30 minutes before use in 3-pentenenitrile hydrocyanation.

General Procedure for Reactions

Hydrocyanation of butadiene: If the catalyst was made according to method A, 0.074 mL of the above catalyst solution nominally containing about 0.0020 mmol Ni is added to each of 2 reaction vials fitted with septum caps. If the catalyst was made by method B the whole catalyst sample as specified is used. The reaction vials are cooled to −20° C. and 120 μL of a solution of HCN in valeronitrile (0.830 mmol HCN) and 280 μL of a solution of butadiene (BD) in toluene (0.925 mmol BD) are added to each vial. The vials are sealed and placed in a hot block reactor set at 80° C. Samples are removed after 3 hours and quenched by cooling to −20° C. The reaction mixtures are then diluted in ethyl ether and the product distribution analyzed by GC against valeronitrile as an internal standard. The results are presented as relative percent of the starting HCN that had been converted to useful nitriles (3-pentenenitrile (3PN), and 2-methyl-3-butenenitrile (2M3BN)).

Isomerization of 2-methyl-3-butene nitrile (2M3BN): If the catalyst was made according to method A, 0.082 mL of the above catalyst solution nominally containing about 0.0022 mmol Ni is added to each of 2 reaction vials fitted with septum caps. If the catalyst was made by method B, the whole catalyst sample as specified is used. 130 μL of a cold solution containing 2M3BN and valeronitrile (0.930 mmol 2M3BN) are added to the reaction vials. The vials are sealed and placed in a hot block reactor set at 125° C. Samples are removed after 3.0 hrs, cooled and diluted in ethyl ether. The product distribution is analyzed by GC using valeronitrile as an internal standard. The results are presented as the 3PN/2M3BN ratio.

Hydrocyanation of 3-pentenenitrile (3PN): If the catalyst was made according to method A, 0.116 mL of the above catalyst solution nominally containing about 0.00312 mmol Ni is added to each of 2 reaction vials fitted with septum caps. If the catalyst was made by method B, the whole catalyst sample as specified is used. 13 μL of a solution of $ZnCl_2$ in 3PN (0.0067 mmol $ZnCl_2$) is added to the catalyst sample in a reaction vial with fitted with a septum cap. The vial is cooled to −20° C. and 125 μL of a solution of HCN, 3PN, and 2-ethoxyethyl ether (0.396 mmol HCN, 0.99 mmol 3PN) are added. The 3PN used for hydrocyanation and hydroformylation contained approximately 97% t-3-pentenenitrile (GC). The vial is sealed and set aside for 24 hours at room temperature. The reaction mixture is diluted with ethyl ether and the product distribution analyzed by GC using 2-ethoxyethyl ether as an internal standard. The results are presented as the relative percent of the starting pentenenitriles that have been converted to dinitrile product and the percent yield based on HCN. The selectivity to the linear adiponitrile (ADN) isomer is reported as percent ADN in reaction product mixture.

Hydrocyanation of 3-pentenenitrile was also performed by slowly adding the HCN to the reaction mixture. The catalyst composition and 3-pentenenitrile were heated in a thermostatically controlled oil bath. HCN was delivered to the flask as an HCN/$N_2$ gas mixture by bubbling dry nitrogen carrier gas through liquid HCN maintained in an ice bath at 0° C. This provided a vapor stream that was about 35% by volume HCN. The rate of nitrogen gas flow determined the rate of HCN delivery. Samples were periodically analyzed by gas chromatography (GC).

Hydroformylation of 3-pentenenitrile: Hydroformylation experiments were performed according to the following procedure. In a drybox, a solution containing 3-pentenenitrile (5.0 g), Rh(CO)$_2$(acac) (2.5 mg), and 1,2-dichlorobenzene (internal standard, 0.27 M) was prepared. This solution was added to a glass-lined pressure vessel containing approximately two molar equivalents of the supported phosphorus compound per equivalent of rhodium. The reactor was sealed, pressurized to 65 psig with a 1:1 molar ratio of CO/$H_2$ and heated to 95° C. for 3 hours. The reactor was cooled and depressurized and a sample of the reaction mixture was analyzed by gas chromatography on an HP 5890A Chromatograph with a DB5 fused silica capillary column (30 meters, 0.32 mm I.D., 0.25 µm film thickness) purchased from J. B. Scientific.

EXAMPLES

Example 1

Aspect 2: Preparation of ethylenically unsaturated, phosphorus-containing bidentate ligand (1): Under nitrogen atmosphere, a 100 mL flask with magnetic stir bar was charged with 2.450 grams of 2,2-bis(4-hydroxy-3-methylphenyl)propane, 0.865 grams of acryloyl chloride, 40 mL of toluene and 8 mL of THF. The mixture was cooled to −30° C. and 1.2 grams of triethylamine in 15 mL of toluene was added. About a quarter of the solvent was removed under vacuum and the mixture cooled to −30° C. To this mixture was added 2.266 grams of the phosphorodichlorodite of 2-isopropylphenol and 1.2 grams of triethylamine in 10 mL of toluene. The mixture was stirred for one and one-half hours and cooled to −30° C. To the mixture was added 1.157 grams of 3,3',5,5'-tetramethyl-2,2'-biphenol and 1.2 grams of triethylamine. The mixture was kept at −30° C. overnight and then filtered. Solvent was removed to give 5.978 grams of a tacky brown solid ($^{31}$P NMR in CDCl$_3$: 142.21, 142.15, 135.20, 135.11, 134.74, 134.29, 132.01, 131.96, and 131.13).

Example 1A

Aspect 9: Preparation of catalyst: 50 mg (0.042 mmol) of the composition comprising ethylenically unsaturated, bidentate phosphorus ligands described in Example 1 were used to prepare catalyst according to Method A. The procedures described above were used to evaluate the hydrocyanation of butadiene, the isomerization of 2M3BN and the hydrocyanation of 3PN.

Aspect 10: Hydrocyanation of butadiene: Analysis showed that 87% of the starting HCN had been converted to useful nitriles, with a 3-pentenenitrile to 2-methyl-3-butenenitrile ratio (3PN/2M3BN) of 1.13.

Aspect 10: Hydrocyanation of 3-pentenenitrile: GC analysis using 2-ethoxyethyl ether as an internal standard showed 19.4% of the starting pentenitriles had been converted to dinitrile product (54% yield based on HCN). The selectivity to the linear ADN isomer was 93.7%.

Aspect 11: Isomerization of 2-methyl-3-butenenitrile: GC analysis with valeronitrile as an internal standard showed 3PN/2M3BN ratio of 1.1.

Example 2

Aspect 3: Polymerization of ethylenically unsaturated ligand (1): To 1.230 grams of the tacky brown solid produced in Example 1 was added 10 mL of toluene and 20 milligrams of 2,2'-azobis(2-methylpropanenitrile), sold by E.I. du Pont de Nemours & Co., Inc. as Vazo®64 free radical initiator. The mixture was heated to 65° C. for two days and 70° C. for one additional day. Acetonitrile was added and the toluene solvent was removed under vacuum. To the residue was added 30 mL of acetonitrile producing a yellow solid. The acetonitrile solvent was decanted off and the residue dried under vacuum ($^{31}$P NMR in CDCl$_3$: 141.43, 134.39, 134.30, 133.97, 133.48, 132.85, and 131.21 and Elemental Analysis: 74.81% C; 6.99% H; 4.31% P).

Example 2A

Aspect 9: Preparation of catalyst: 50 mg (0.042 mmol) of the polymer in Example 2 was used to prepare catalyst according to Method A.

The procedures described above were used to evaluate the hydrocyanation of BD, the isomerization of 2M3BN and the hydrocyanation of 3PN.

Aspect 10: Hydrocyanation of butadiene: Analysis showed that 86.2% of the starting HCN had been converted to useful nitriles (3PN/2M3BN=1.6).

Aspect 10: Hydrocyanation of 3-pentenenitrile: GC analysis using 2-ethoxyethyl ether as an internal standard showed 33.2% of the starting pentenitriles had been converted to dinitrile product (92% yield based on HCN). The selectivity to the linear ADN isomer was 93.3%.

Aspect 11: Isomerization of 2-methyl-3-butenenitrile: GC analysis with valeronitrile as an internal standard indicated 3PN/2M3BN ratio of 16.3.

Example 2B

Aspect 12: Hydroformylation of 3PN using the polymeric phosphite described in Example 2: GC analysis indicated 34% conversion of 3PN to a mixture containing the monoaldehydes and valeronitrile; selectivity to 5-formylvaleronitrile: 16% on a mole basis; linearity of aldehydes produced: 19%.

Example 3

Aspect 3: Copolymerization of ethylenically unsaturated ligand (1) with methyl acrylate: To 0.760 grams of the tacky brown solid from Example 1 was added 10 mL of toluene, 55 milligrams of methyl acrylate and 20 milligrams of Vazo®64 free radical initiator. The mixture was heated at 65° C. for 2 days and 70° C. for one additional day. The toluene solvent was removed under vacuum and 30 mL of acetonitrile was added. The acetonitrile solvent was decanted and the yellow solid dried under vacuum ($^{31}$P NMR in CDCl$_3$: 142.22, 135.21, 135.13, 134.78, 134.32, 133.63, 132.04, and 131.30 and Elemental Analysis: 73.56% C; 7.09% H; 4.61% P).

Example 3A

Aspect 9: Preparation of catalyst: 54 mg (0.042 mmol) of the polymer in Example 3 was used to prepare catalyst according to Method A.

The procedures described above were used to evaluate the hydrocyanation of BD, the isomerization of 2M3BN and the hydrocyanation of 3PN.

Aspect 10: Hydrocyanation of butadiene: Analysis showed that 86.1% of the starting HCN had been converted to useful nitriles (3PN/2M3BN=2.0).

Aspect 10: Hydrocyanation of 3-pentenenitrile: GC analysis using 2-ethoxyethyl ether as an internal standard showed 32.7% of the starting pentenitriles had been converted to dinitrile product (90.3% yield based on HCN). The selectivity to the linear ADN isomer was 93.3%.

Aspect 11: Isomerization of 2-methyl-3-butenenitrile: GC analysis with valeronitrile as an internal standard indicated 3PN/2M3BN ratio of 15.6.

Example 3B

Aspect 12: Hydroformylation of 3PN with the polymeric phosphite described in Example 3: GC analysis indicated 33% conversion of 3PN to a mixture containing the monoaldehydes and valeronitrile; selectivity to 5-formylvaleronitrile: 31% on a mole basis; linearity of aldehydes produced: 39%.

Example 4

Aspect 3: Copolymerization of ethylenically unsaturated ligand (1) with bisphenol A dimethacrylate: To 0.650 grams of the tacky brown solid from Example 1 was added 10 mL of toluene and 199 milligrams of bisphenol A dimethacrylate and 20 milligrams of Vazo®64 free radical initiator. The mixture was heated at 65° C. for 2 days and 70° C. for one additional day. The toluene solvent was removed under vacuum and 30 mL of acetonitrile was added. The acetonitrile solvent was decanted and the remaining polymeric yellow solid was dried under vacuum. The solid swells in CDCl$_3$ but appears insoluble.

Aspect 9: Preparation of catalyst: To 0.725 g of the above yellow solid was added 4 mL of toluene. The mixture was stirred for 30 minutes and then 87 mg of Ni(COD)$_2$ and an additional 4 mL of toluene were added. The mixture was stirred for one hour before removing the solvent under reduced pressure.

Example 4A

Fourteen mg of the catalyst prepared in Example 4 was used for each screen. The procedures described above were used to evaluate the hydrocyanation of BD, the isomerization of 2M3BN and the hydrocyanation of 3PN.

Aspect 10: Hydrocyanation of butadiene: Analysis showed that 72.9% of the starting HCN had been converted to useful nitriles (3PN/2M3BN=7.78).

Aspect 10: Hydrocyanation of 3-Pentenenitrile: GC analysis using 2-ethoxyethyl ether as an internal standard showed 30.3% of the starting pentenitriles had been converted to dinitrile product (84% yield based on HCN). The selectivity to the linear ADN isomer was 94.0%.

Aspect 11: Isomerization of 2-methyl-3-butenenitrile: GC analysis with valeronitrile as an internal standard indicated 3PN/2M3BN ratio of 15.2.

Example 5

Aspect 3: Copolymerization of ethylenically unsaturated ligand (1) with the diacrylate of 2,2-bis(4-hydroxy-3-methylphenyl)propane: To 0.640 grams of the tacky brown solid from Example 1 was added 10 mL of toluene, 0.196 grams of the diacrylate of 2,2-bis(4-hydroxy-3-methylphenyl)propane and 20 milligrams of Vazo®64 free radical initiator. The mixture was heated at 65° C. for 2 days and 70° C. for one additional day. The toluene solvent was removed under vacuum and 30 mL of acetonitrile was added. The acetonitrile solvent was decanted and the yellow polymeric solid was dried under vacuum. The solid swells in CDCl$_3$ but appears insoluble.

Aspect 9: Preparation of catalyst: To 0.707 g of the solid from Example 5 was added 4 mL of toluene. After stirring for 30 minutes, 85 mg of Ni(COD)$_2$ was added. An additional 4 mL of toluene was added and the mixture was stirred for one hour. The solvent was removed under vacuum and the residue vacuum dried.

Example 5A

Fourteen mg of the catalyst prepared in Example 5 was used for each screen. The procedures described above were used to evaluate the hydrocyanation of BD, the isomerization of 2M3BN and the hydrocyanation of 3PN.

Aspect 10: Hydrocyanation of butadiene: Analysis showed that 80.4% of the starting HCN had been converted to useful nitriles (3PN/2M3BN=4.95).

Aspect 10: Hydrocyanation of 3-pentenenitrile: GC analysis using 2-ethoxyethyl ether as an internal standard showed 31.3% of the starting pentenitriles had been converted to dinitrile product (86% yield based on HCN). The selectivity to the linear ADN isomer was 94.5%.

Aspect 11: Isomerization of 2-methyl-3-butenenitrile: GC analysis with valeronitrile as an internal standard indicated 3PN/2M3BN ratio of 15.5.

Example 5B

Aspect 12: Hydroformylation of 3PN with the polymeric phosphite described in Example 5: GC analysis indicated 26% conversion of 3PN to a mixture containing the monoaldehydes and valeronitrile; selectivity to 5-formylvaleronitrile: 34% on a mole basis; linearity of aldehydes produced: 45%.

Example 6

Aspect 2: Preparation of ethylenically unsaturated ligand (6): A flask with a magnetic stir bar was charged with 0.248 grams of the phosphorodichlorodite of o-cresol, 0.391 grams of the monoacrylate of 2,2-bis(4-hydroxy-3-methylphenyl) propane (derived from the reaction of acryloyl chloride with 2,2-bis(4-hydroxy-3-methylphenyl)propane) and 15 mL of toluene). The mixture was cooled to −30° C. and a precooled solution of triethylamine (0.212 g) in 10 mL of toluene was added. The slurry was stirred for 2 hours. $^{31}$P NMR of the solution: 162.91 (major peak) with minor peaks at 165.46 and 161.65. The mixture was cooled to −30° C.

and 0.206 g of 3,3'-diisopropyl-5,5',6,6'-tetramethyl-2,2'-biphenol was added. More triethylamine was added (0.2 g). The mixture was stirred overnight and then filtered and solvent removed to give 0.765 grams of tacky opaque solid ($^{31}$P NMR (CDCl$_3$): 135.45, 135.17, 135.13, 135.03, 132.84, 132.76, 132.67, 132.56, 132.51, 132.45, 132.35, 132.27, 132.07, 131.98, 127.75, and 127.70).

Example 6A

Aspect 9: Preparation of catalyst: 51 mg (0.042 mmol) of the composition comprising monomeric bidentate phosphorus ligands in Example 6 was used to prepare catalyst according to Method A.

The procedures described above were used to evaluate the hydrocyanation of BD, the isomerization of 2M3BN and the hydrocyanation of 3PN.

Aspect 10: Hydrocyanation of butadiene: Analysis showed that 88.0% of the starting HCN had been converted to useful nitriles (3PN/2M3BN=0.87).

Aspect 10: Hydrocyanation of 3-pentenenitrile: GC analysis using 2-ethoxyethyl ether as an internal standard showed 21.5% of the starting pentenitriles had been converted to dinitrile product (59% yield based on HCN). The selectivity to the linear ADN isomer was 95.8%.

Aspect 11: Isomerization of 2-methyl-3-butenenitrile: GC analysis with valeronitrile as an internal standard indicated 3PN/2M3BN ratio of 2.05.

Example 7

Aspect 3: Polymerization of ethylenically unsaturated ligand (6): To 0.700 grams of the tacky opaque solid produced in Example 6 was added 10 mL of toluene. The mixture was cooled to −30° C. and 20 milligrams of Vazo®64 free radical initiator were added. The mixture was heated at 65° C. for two days and then 70° C. for one additional day. The toluene solvent was removed in vacuum and 30 mL of acetonitrile was added. The acetonitrile solution was decanted and the residue dried under vacuum to give a white solid (Elemental Analysis: 74.30% C; 7.35% H; 4.34% P).

Example 7A

Aspect 9: Preparation of catalyst: 51 mg (0.042 mmol) of the polymer from Example 7 was used to prepare catalyst according to Method A.

The procedures described above were used to evaluate the hydrocyanation of BD, the isomerization of 2M3BN and the hydrocyanation of 3PN.

Aspect 10: Hydrocyanation of butadiene: Analysis showed that 86.1% of the starting HCN had been converted to useful nitrites (3PN/2M3BN=0.76).

Aspect 10: Hydrocyanation of 3-pentenenitrile: GC analysis using 2-ethoxyethyl ether as an internal standard showed 32.6% of the starting pentenitriles had been converted to dinitrile product (90% yield based on HCN). The selectivity to the linear ADN isomer was 89.0%.

Aspect 11: Isomerization of 2-methyl-3-butenenitrile: GC analysis with valeronitrile as an internal standard indicated 3PN/2M3BN ratio of 16.5.

Example 7B

Aspect 12: Hydroformylation of 3-pentenenitrile with the polymeric phosphite described in Example 7: GC analysis indicated 41% conversion of 3PN to a mixture containing the mono-aldehydes and valeronitrile; selectivity to 5-formylvaleronitrile: 54% on a mole basis; linearity of aldehydes produced: 71%.

Example 8

Aspect 2: Preparation of ethylenically unsaturated ligand (8): Under nitrogen, a 100 mL flask with magnetic stir bar was charged with 1.880 grams of 2,2-bis(4-hydroxy-3-methylphenyl)propane, 0.664 grams of acryloyl chloride, and 40 mL of THF. The mixture was cooled to −30° C. and a pre-cooled solution (at −30° C.) containing 1 gram of triethylamine in 15 mL of THF was added. The THF was removed under vacuum and the residue dissolved in 50 mL of THF. To this slurry was added 0.503 grams of phosphorus trichloride. The mixture was cooled to −30° C. and a pre-cooled solution containing 0.5 gram of triethylamine in 10 mL of THF was added. After stirring for several days, 0.598 grams of 3,3'-diisopropyl-5,5',6,6'-tetramethyl-2,2'-biphenol was added along with 1.2 grams of triethylamine. The mixture was stirred for forty minutes, filtered and the solvent was removed under vacuum to give 3.146 grams of a yellow solid ($^{31}$P NMR (CDCl$_3$): 135.58, 135.25, 135.18, 134.80, 134.71, 132.71, 131.90, 130.80, 127.94, and 127.87).

Example 8A

Aspect 9: Preparation of catalyst: 68 mg (0.042 mmol) of the composition comprising monomeric bidentate phosphorus ligands in Example 8 was used to prepare catalyst according to Method A. The procedures described above were used to evaluate the hydrocyanation of BD, the isomerization of 2M3BN and the hydrocyanation of 3PN.

Aspect 10: Hydrocyanation of butadiene: Analysis showed that 84.8% of the starting HCN had been converted to useful nitriles (3PN/2M3BN=0.51).

Aspect 10: Hydrocyanation of 3-pentenenitrile: GC analysis using 2-ethoxyethyl ether as an internal standard showed 31.0% of the starting pentenitriles had been converted to dinitrile product (86% yield based on HCN). The selectivity to the linear ADN isomer was 92.8%.

Aspect 11: Isomerization of 2-methyl-3-butenenitrile: GC analysis with valeronitrile as an internal standard indicated 3PN/2M3BN ratio of 2.0.

Example 9

Aspect 3: Polymerization of ethylenically unsaturated ligand (8): To 0.700 grams of the monomeric yellow solid from Example 8 was added 1 mL of toluene and 20 milligrams of Vazo®64 free radical initiator, and 0.2 mL of THF. The mixture was heated at 70° C. for one day. Solvent was removed and the yellow polymerized solid was collected.

Aspect 9: Preparation of nickel catalyst: To 565 milligrams of the above polymeric solid was added 2 mL of toluene and 64 milligrams of Ni(COD)$_2$. Another 1 mL of toluene was added and the slurry was stirred for 2 hours. The mixture was stored overnight in a −30° C. freezer and then the toluene solvent was decanted and the solid vacuum dried.

Example 9A

Fifteen mg of catalyst from Example 9 was used for each screen. The procedures described above were used to evaluate the hydrocyanation of BD, the isomerization of 2M3BN and the hydrocyanation of 3PN.

Aspect 10: Hydrocyanation of butadiene: Analysis showed that 75.0% of the starting HCN had been converted to useful nitrites (3PN/2M3BN=2.35).

Aspect 10: Hydrocyanation of 3-pentenenitrile: GC analysis using 2-ethoxyethyl ether as an internal standard showed 30.9% of the starting pentenitriles had been converted to dinitrile product (85% yield based on HCN). The selectivity to the linear ADN isomer was 92.2%.

Aspect 11: Isomerization of 2-methyl-3-butenenitrile: GC analysis with valeronitrile as an internal standard indicated 3PN/2M3BN ratio of 15.8.

Example 10

Aspect 3: Copolymerization of ethylenically unsaturated ligand (8) with methyl acrylate: To 0.600 grams of the yellow solid from Example 8 was added 1 mL of toluene, 0.032 grams of methyl acrylate, 20 milligrams of Vazo®64 free radical initiator, and 0.2 mL of THF. The mixture was heated at 70° C. for one day. The toluene solvent was removed and the yellow solid was collected.

Aspect 9: Preparation of nickel catalyst: To 550 milligrams of the above solid was added 3 mL of toluene and the mixture was stirred for 30 minutes. To this mixture was added 59 milligrams of Ni(COD)$_2$. The resulting red slurry was stirred for 45 minutes, the toluene solvent was removed under vacuum, and the remaining solid was vacuum dried.

Example 10A

Fifteen mg of the catalyst from Example 10 was used for each screen. The procedures described above were used to evaluate the hydrocyanation of BD, the isomerization of 2M3BN, and the hydrocyanation of 3PN.

Aspect 10: Hydrocyanation of butadiene: Analysis showed that 70.6% of the starting HCN had been converted to useful nitriles (3PN/2M3BN=2.58).

Aspect 10: Hydrocyanation of 3-pentenenitrile: GC analysis using 2-ethoxyethyl ether as an internal standard showed 30.6% of the starting pentenitriles had been converted to dinitrile product (85% yield based on HCN). The selectivity to the linear ADN isomer was 92.3%.

Aspect 11: Isomerization of 2-methyl-3-butenenitrile: GC analysis with valeronitrile as an internal standard indicated 3PN/2M3BN ratio of 15.2.

Example 11

Aspect 3: Copolymerization of ethylenically unsaturated ligand (8) with bisphenol A dimethacrylate: To 0.600 grams of the yellow solid from Example 8 was added 1 mL of toluene, 0.134 grams of bisphenol A dimethacrylate, 20 milligrams of Vazo®64 free radical initiator, and 0.2 mL of THF. The mixture was heated at 70° C. for one day. The THF solvent was removed and the yellow solid was collected.

Aspect 9: Preparation of nickel catalyst: To 675 milligrams of the above solid was added 3 mL of toluene and the mixture was stirred for 30 minutes. To this mixture was added 62 milligrams of Ni(COD)$_2$. The red slurry was stirred for 30 minutes, the toluene solvent was removed under vacuum, and the solid was vacuum dried.

Example 11A

Eighteen mg of the catalyst from Example 11 was used for each screen. The procedures described above were used to evaluate the hydrocyanation of BD, the isomerization of 2M3BN, and the hydrocyanation of 3PN.

Aspect 10: Hydrocyanation of butadiene: Analysis showed that 75.3% of the starting HCN had been converted to useful nitriles (3PN/2M3BN=3.04).

Aspect 10: Hydrocyanation of 3-pentenenitrile: GC analysis using 2-ethoxyethyl ether as an internal standard showed 30.3% of the starting pentenitriles had been converted to dinitrile product (84% yield based on HCN). The selectivity to the linear ADN isomer was 91.5%.

Aspect 11: Isomerization of 2-methyl-3-butenenitrile: GC analysis with valeronitrile as an internal standard indicated 3PN/2M3BN ratio of 15.9.

Example 11B

Aspect 10: Semibatch 3-pentenenitrile hydrocyanation using nickel catalyst: A reaction mixture of 0.567 grams of the above catalyst, 0.027 grams of zinc chloride, 5 mL of toluene and 5 mL of 3PN in a closed reactor was placed in a 50° C. oil bath and HCN saturated nitrogen was delivered at a nitrogen flow rate of 24 cc/min. The reaction was heated at 50° C. for 1 hour and then at 70° C. for 30 minutes. Nitrogen flow was decreased to 12 cc/min. and the reaction was run at 70° C. for an additional 90 minutes. The temperature was then increased to 80° C. and the reaction was continued for another 90 minutes. GC analysis indicated 68% conversion of 3-pentenenitrile to dinitrile with an ADN selectivity of 89%.

Example 12

Aspect 2: Preparation of ethylenically unsaturated ligand (12): Under nitrogen, a 100 mL flask with magnetic stir bar was charged with 0.931 grams of the monoacrylate of 2,2-bis(4-hydroxy-3-methylphenyl)propane (prepared from the reaction of acryloyl chloride with 2,2-bis(4-hydroxy-3-methylphenyl)propane), 0.627 grams of the phosphorodichloridite of o-cresol, and 40 mL of toluene. The mixture was cooled to −30° C. and a precooled solution (at −30° C.) containing 0.4 grams of triethylamine in 15 mL of toluene was added. After stirring for 2 hours, $^{31}$P NMR in CDCl$_3$ indicated a peak at 162.8 ppm. The mixture was cooled to −30° C. and 0.448 grams of 3,3',4,4',5,5'-hexamethyl-2,2'-biphenol and 0.65 grams of triethylamine in 2 mL of THF were added. After stirring overnight, the mixture was filtered and the THF removed under vacuum to give a yellow solid. The solid was dissolved in 10 mL of toluene and 0.8 grams of triethylamine was added in 5 mL of THF. The mixture was stirred overnight and filtered. The solvent was removed. $^{31}$P NMR indicated some phosphorodichloridite still present. The residue was dissolved in THF and 0.75 grams of triethylamine were added. After stirring overnight, the mixture was filtered through silica gel, and the solvent was removed under vacuum. 1.225 Grams of yellow solid were recovered ($^{31}$P NMR in CDCl$_3$: 137.47, 137.31, 135.29, 135.21, 135.15, 135.00, 134.82, 134.73, 134.40, 134.31, 133.41, 133.40, 132.07, 131.98, 130.44, 127.74, and 127.69).

Example 12A

Aspect 9: Preparation of catalyst: 50 mg (0.042 mmol) of the composition comprising monomeric bidentate phosphorus ligands prepared as in Example 12 were used to prepare catalyst according to Method A.

The procedures described above were used to evaluate the hydrocyanation of BD, the isomerization of 2M3BN, and the hydrocyanation of 3PN.

Aspect 10: Hydrocyanation of butadiene: Analysis showed that 80.0% of the starting HCN had been converted to useful nitriles (3PN/2M3BN 0.95).

Aspect 10: Hydrocyanation of 3-pentenenitrile: GC analysis using 2-ethoxyethyl ether as an internal standard showed 26.8% of the starting pentenitriles had been converted to dinitrile product (74% yield based on HCN). The selectivity to the linear ADN isomer was 95.5%.

Aspect 11: Isomerization of 2-methyl-3-butenenitrile: GC analysis with valeronitrile as an internal standard indicated 3PN/2M3BN ratio of 4.0.

Example 12B

Aspect 3: Polymerization of ethylenically unsaturated ligand (12): To 0.657 grams of the yellow monomeric solid produced in Example 12 was added 0.9 mL of toluene, 100 mL of THF and 20 milligrams of Vazo®64 free radical initiator. The mixture was heated at 70° C. for one day. Solvent was removed and the yellow polymeric solid was collected.

Aspect 9: Preparation of nickel catalyst: To 375 milligrams of the above polymeric solid was added 5 mL of toluene and 58 milligram of $Ni(COD)_2$. The mixture was stirred overnight.

Aspect 10: Hydrocyanation of 3-pentenenitrile: 29 milligrams of $ZnCl_2$ and 5 mL of 3PN were added to the mixture. The mixture was heated in a 50° C. oil bath and HCN was delivered with 24 cc/min. nitrogen flow rate. After 90 minutes of reaction, GC analysis indicated 57.6% conversion of 3PN with 92% selectivity to ADN. To the mixture was added 5 mL of 3PN and the reaction was continued for 90 minutes. At this point, HCN delivery was stopped but the reaction was allowed to continue at 50° C. for 120 minutes. The mixture was allowed to sit under nitrogen at room temperature overnight. GC analysis indicated 62% conversion of 3PN with 91.3% selectivity to ADN.

Ligand recycle: At this time, the solvent was removed via syringe from the reactor. 5 mL of toluene, 5 mL of 3PN and 29 milligrams of $ZnCl_2$ were added to begin an additional reaction. The reaction was placed in a 70° C. oil bath and HCN was delivered with a nitrogen flow rate of 30 cc/min. The reaction was then stored at room temperature overnight. The mixture was then heated at 70° C. oil bath with HCN delivered with a nitrogen flow rate of 30 cc/min for 30 minutes. GC analysis indicated 75% conversion of 3PN with selectivity to ADN of 92.2%. To this mixture was added 5 mL of 3PN. The mixture was heated at 70° C. oil bath with HCN delivered with a nitrogen flow rate of 30 cc/min for 210 minutes. GC analysis indicated 65% conversion of 3PN with selectivity to ADN of 91.8%.

Example 12C

Aspect 9: Preparation of nickel catalyst: To 179 mg of the solid from the polymer prepared as in Example 12B was added 15 mL of THF. The mixture was stirred overnight and then 27.5 mg of $Ni(COD)_2$ was added. The solvent was removed under vacuum and the residue was vacuum dried.

Eleven mg of the catalyst from above was used for each screen. The procedures described above were used to evaluate the hydrocyanation of BD and the isomerization of 2M3BN.

Aspect 10: Hydrocyanation of butadiene: Analysis showed that 54% of the starting HCN had been converted to useful nitriles (3PN/2M3BN=1.1).

Aspect 11: Isomerization of 2-methyl-3-butenenitrile: GC analysis with valeronitrile as an internal standard indicated 3PN/2M3BN ratio of 18.5.

Example 13

Preparation of 6,6'-divinyl-2,2'-dihydroxy-1,1'-binaphthyl:

A solution of 6,6'-dibromo-2,2'-dihydroxy-1,1'-binaphthyl (0.694 g, 1.56 mmol), $Pd(OAc)_2$ (0.020 g, 5 mol %), $P(o-tolyl)_3$ (0.080 g, 15 mol %) and $Et_3N$ (0.5 mL) in DMF (2 mL) was pressurized with ethylene (200 psi) at 750 C for 18 hrs. The resulting mixture was diluted in ethyl acetate (20 mL) and filtered through celite, followed by water (20 mL) and brine (20 mL) washes. The solution was dried over $MgSO_4$ and evaporated to produce a tan solid, which was purified by column chromatography to yield the desired product in 54% yield (0.286 g).

Aspect 2: Preparation of the diphosphite ligand (13): Under an atmosphere of nitrogen, a cold (−30° C.) $Et_2O$ (5 mL) solution of 6,6'-divinyl-2,2'-dihydroxy-1,1'-binaphthyl (0.051 g, $1.5 \times 10^{-4}$ mol) and $Et_3N$ (0.040, $3.9 \times 10^{-4}$ mol) was slowly added to a $Et_2O$ (5 mL) solution of phosphorochlorodite of 2-isopropoxyphenol (0.140 g, $3.9 \times 10^{-4}$ mol). The solution was allowed to warm up to room temperature and was stirred for one hour. The reaction mixture was filtered through celite and alumina. The volatiles were evaporated to yield a white powder in 67% yield. (0.100 g).

Example 13A

Aspect 3: Polymerization of the ethylenically unsaturated compound (13) with divinylbenzene: Under an atmosphere of nitrogen, a vial fitted with a Teflon® fluoropolymer resin screwcap was charged with the diphosphite (0.027 g, $2.7 \times 10^{-5}$ mol) described in example 13, AIBN (0.002 g), DVB (0.1900 g) and THF (0.184 g). This vial was screwed shut and placed in a 70° C. oil bath for 24 hours. After polymerization, the polymer was crushed and the volatiles were removed under vacuum. The resulting white polymer (0.350 g) was insoluble in all organic solvents. Elemental analysis: P found: 1.51%.

Aspect 9: Preparation of nickel catalyst: A mixture of toluene (1 mL) and $Ni(COD)_2$ (0.020 g) was added to the above polymer. The white polymer immediately turned yellow-orange. After stirring approximately one minute, the solution was filtered from the loaded polymer. The yellow-orange polymer was rinsed with THF (2×3 mL) and dried under vacuum.

Aspect 10: Hydrocyanation of 3-pentenenitrile: A sample (0.052 g polymer, 0.042 mmol diphosphite) was evaluated for hydrocyanation of 3PN using the procedure described above. GC analysis using 2-ethoxyethyl ether as an internal standard showed 27.5% of the starting pentenitriles had been converted to dinitrile product (76% yield based on HCN). The selectivity to the linear ADN isomer was 92.1%.

Example 14

Aspect 2: Preparation of ethylenically unsaturated diphosphite ligand (14): Under an atmosphere of nitrogen, a cold (−30° C.) $Et_2O$ (5 mL) solution of 3,3',4,4',5,5',6,6'-octamethyl-2,2'-dihydroxy-1,1'-biphenyl (0.100 g, 0.67 mmol) and $Et_3N$ (0.152 g, 1.5 mmol) was slowly added to an $Et_2O$ (5 mL) solution of phosphorochlorodite of trans-2-ethoxy-5-(1-propenyl)phenol (0.631 g, 1.5 mmol). The solution was allowed to warm to room temperature and was stirred for one hour. The reaction mixture was filtered through celite and alumina. The volatiles were evaporated to give 86% yield of a white powder (0.623 g).

Example 14A

Aspect 3: Polymerization of the ethylenically unsaturated compound (14) with divinylbenzene and styrene: Under an atmosphere of nitrogen, a vial fitted with a Teflon® fluoropolymer resin screwcap was charged with the diphosphite (0.100 g, 0.09 mmol) described in example 14, AIBN (0.005 g), DVB (0.40 g), styrene (0.70 g) and THF (1.5 mL). This vial was screwed shut and placed in a 70° C. oil bath for 48 hours, after which DVB (0.75 g) and AIBN (0.005 g) were added and the vial was returned to the oil bath. After 48 hours, the opaque polymer was crushed and the volatiles were removed under vacuum. The resulting white polymer (0.137 g) was insoluble in all organic solvents.

Aspect 9: Preparation of nickel catalyst. A mixture of toluene (1 mL) and Ni(oTTP)$_3$ (0.112 g) was added to the above polymer. The white polymer immediately turned yellow-orange. After stirring approximately one minute, the solution was filtered from the loaded polymer. The yellow-orange polymer was rinsed with THF (2×3 mL) and dried under vacuum.

Example 14B

Aspect 8: Hydrocyanation of butadiene: A solution of HCN was prepared by mixing 5 g of HCN with 15 g of valeronitrile. A butadiene solution was prepared by mixing 2 g of butadiene with 6 g of toluene. To 30 mg of the nickel catalyst prepared in example 14A was added 0.28 mL of the butadiene solution and 0.12 mL of the HCN solution. The mixture was heated at 80° C. for 3 hours. GC analysis indicated 81% 3-pentenenitrile and 5.7% 2-methyl-3-butenenitrile.

Example 15

Aspect 5.1: Polymerization of 6,6'-divinyl-2,2'-dihydroxy-1,1'-binaphthyl with styrene: Under nitrogen atmosphere, a vial fitted with a Teflon® fluoropolymer resin screwcap was charged with 6,6'-divinyl-2,2'-dihydroxy-1,1'-binaphthyl (0.500 g, 1.48 mmol), AIBN (0.040 g), styrene (4.0 mL) and THF (4.0 mL). The vial was screwed shut and placed in a 70° C. oil bath for 24 hours. After polymerization, the polymer was crushed and the volatiles were removed under vacuum. The resulting white polymer (4.8 g) was insoluble in all organic solvents.

Example 16

Aspect 5.2: Formation of the diphosphite ligand from the polymeric precursor of Example 15: Under nitrogen atmosphere, a cold solution (–30° C.) of o-cresol (0.027 g, 0.25 mmol) in toluene (5 mL) was added to a solution of the phosphorodichlorodite of phenol (0.045 g, 0.25 mmol) and n-Bu$_3$N (0.047 g, 0.25 mmol) in toluene (5 mL). The resulting mixture was allowed to stir at room temperature for 1.5 hours, after which it was cooled to –30° C. This cold solution was added to a cold slurry of polymer from example 15 (0.328 g, 0.10 mmol) and n-Bu$_3$N (0.047 g, 0.25 mmol) in toluene (5 mL). This mixture was stirred at room temperature for five hours. The polymer product was isolated by filtration and washed with toluene and acetonitrile. After drying under vacuum, a tacky solid (0.350 g) was obtained.

Aspect 9: Preparation of nickel catalyst: This polymer (0.186 g) was mixed with toluene (3 mL) and cooled (–30° C.) for 30 minutes, after which a cold solution of Ni(oTTP)$_3$ (0.055 g) in toluene (3 mL) was added and allowed to stir at room temperature for 20 minutes. The resulting yellow-orange solid (0.140 g) was isolated by filtration and dried under vacuum.

Example 16A

Aspect 10: Hydrocyanation of BD with nickel catalyst prepared in Example 16: A solution of HCN was prepared by mixing 5 g of HCN with 15 g of valeronitrile. A butadiene solution was prepared by mixing 2 g of butadiene with 6 g of toluene. To 44 mg of the nickel catalyst prepared in example 16 was added 0.28 mL of the butadiene solution and 0.12 mL of the HCN solution. The mixture was heated at 80° C. for 2 hours. GC analysis indicated 8% 3-pentenenitrile and 5% 2-methyl-3-butenenitrile.

Example 17

Aspect 2: Preparation of ethylenically unsaturated, phosphorus-containing bidentate ligand (17): A 500 mL flask with a magnetic stirbar was charged with 8.500 g of 2,2-bis(4-hydroxy-3-methylphenyl)propane and 3.001 g of acryloyl chloride in 120 mL of THF. A solution of triethylamine (3.542 g) in 30 mL of THF was added to the colorless solution dropwise over 60 minutes. The slurry was stirred at room temperature for four hours. Based on peak area, GC on a DB5 column indicated 22% starting diol, 51% monoacrylate and 25% diacrylate. The mixture was cooled to –30° C., and 1.821 g of phosphorus trichloride and 1.386 g of the phosphorochloridite of o-cresol in 10 mL of THF were added. A precooled solution (–30° C.) of triethylamine in 30 mL of THF was added to this mixture dropwise over sixty minutes. After stirring the mixture at room temperature for two hours, $^{31}$P NMR indicated major peaks at 161.96 and 161.77 with minor peaks at 182.44, 131.04 and 126.71. The slurry was cooled back to –30° C. and 3.248 g of 3,3'-diisopropyl-5,5',6,6'-tetramethyl-2,2'-dihydroxy-1,1'-biphenyl and 3.2 g of triethylamine were added. The mixture was stirred at room temperature for 2.5 hours. $^{31}$P NMR indicated a major peak at 131.82 and minor peaks at 134.62, 134.50, 134.23, 131.08 and 130.99. The slurry was filtered through celite, washed with THF, and the solvent was removed by vacuum. The residue was vacuum dried to give 14.866 g of off-white solid. Elemental analysis: 3.70% P.

Example 17A

Aspect 9: Preparation of catalyst: 7 mL of toluene and 110 g of Ni(COD)$_2$ were added to 1.000 g of the solid from Example 17. The mixture was stirred for an hour and the solvent was removed by vacuum.

Example 17B

Aspect 3: Polymerization of nickel catalyst: To the residue from Example 17A was added 1.0 mL of toluene and 20 mg of Vazo 64 free radical initiator. The mixture was heated at 60° C. overnight. The hard yellow solid was crushed and heated at 60° C. for another two hours. The solvent was removed by vacuum and 10 mL of acetonitrile was added to the residue. After stirring for 25 minutes, the solid was filtered, washed with acetonitrile and diethyl ether and vacuum dried to give 1.048 g of yellow solid.

Example 17C

Aspect 10: Hydrocyanation of butadiene: To 13 mg of the catalyst from example 17B was added 1.045 mL of a solution containing butadiene and HCN. The solution was prepared by mixing 6.734 g valeronitrile, 6.572 g 3-pentenenitrile, 5.476 g butadiene, and 2.187 g of HCN. The mixture was heated at 80° C. for 2 hours. GC indicated 38% conversion to nitriles with 3PN/2M3BN of 0.53.

Example 17D

Aspect 11: Isomerization of 2-methyl-3-butenenitrile: To 13 mg of the catalyst from Example 17B was added 0.266 mL of 2M3BN in valeronitrile solution (prepared by mixing 20.7 g 2M3BN and 1.8 g of valeronitrile). The mixture was heated at 80° C. for 2 hours and then heated at 100° C. for one hour. GC indicated 3PN/2M3BN of 0.6.

Example 18

Aspect 2: Preparation of ethylenically unsaturated, phosphorus-containing bidentate ligand (18): A mixture containing bidentate phosphite was prepared similarly to that of Example 17. A 500 ml flask was charged with a stir bar, 8.204 g of 2,2-bis(4-hydroxy-3-methylphenyl)propane, 2.896 g of acryloyl chloride and 175 mL of THF. The mixture was cooled to −30 C and then a precooled solution (−30 C) of triethylamine (3.490 g) in 50 mL of THF was added dropwise over 40 minutes. The slurry was warmed to room temperature and stirred for 90 minutes. Based on peak area, GC indicated 26% starting diol, 45% monoacrylate and 26% diacrylate. The mixture was filtered through celite and washed with THF. The solution was concentrated to 160 mL by removing solvent under vacuum. To 40 mL of this solution was added 440 mg of phosphorus trichloride and 334 mg of the phosphorochloridite of o-cresol in 10 mL of THF. The mixture was cooled to −30 C and a precooled solution (−30 C) of triethylamine (950 mg) in 10 mL of THF was added. The mixture was stirred at room temperature for 30 minutes. To this mixture was added 784 mg of 3,3'-diisopropyl-5,5',6,6'-tetramethyl-2,2'-dihydroxy-1,1'-biphenyl and 1.2 g triethylamine. The mixture was stirred overnight. $^{31}$P NMR indicated peaks at 135.07, 135.01, 134.90, 132.23, 131.48, 131.38 ppm. The slurry was filtered through celite, washed with THF, the solvent was removed by vacuum and the solid was dried under vacuum. A tan solid (3.473 g) was obtained.

Example 18A

Aspect 3: Polymerization of ethylenically unsaturated ligand (18): The solid was dissolved in 6 mL of toluene and 30 mg of Vazo 64 free radical initiator. The mixture was heated at 50° C. for six hours and then held at 60° C. overnight. The solid was crushed and heated at 70° C. for three hours. The solvent was removed by vacuum and the solid was filtered, washed with diethyl ether and vacuum dried to give 3.483 g of yellow solid. Elemental analysis: 3.72% P.

Example 18B

Aspect 9: Preparation of catalyst: The nickel catalyst was prepared from the polymeric ligand described in Example 18A. To 3.28 g of the polymer ligand was added 43 mL of THF. The mixture was stirred overnight and then 361 mg of Ni(COD)$_2$ was added. The mixture was stirred for one hour and the solid was vacuum dried for 3.5 hours and 20 mL of 3PN added. The solid was filtered and washed with 3PN, and acetonitrile and vacuum dried to give 3.170 g of yellow solid.

Example 18C

Aspect 10: Hydrocyanation of butaediene: To 15 mg of the catalyst prepared in Example 18B were added 0.280 mL of a solution containing butadiene (prepared by mixing 6.8 g toluene and 2.0 g butadiene) and 0.120 mL of a solution containing HCN (prepared by mixing 5 g HCN and 15 g of valeronitrile). The mixture was heated at 80° C. for 2 hours. GC analysis indicated 69% conversion to nitriles with a 3PN/2M3BN of 28.

Example 18D

Aspect 11: Isomerization of 2-methyl-3-butenenitrile: To 15 mg of the catalyst prepared in example 18B was added 0.266 mL of a solution of 2M3BN in valeronitrile (prepared by mixing 20.7 g 2M3BN and 1.8 g of valeronitrile). The mixture was heated to 100 C for one hour. GC indicated 3PN/2M3BN ratio of 20.1.

Example 18E

Aspect 10: Semi-batch hydrocyanation of 3-pentenenitrile: To 0.388 g of the catalyst from Example 18B was added 19 mg of zinc chloride and 5 mL of 3PN. The mixture was heated in a 70 C oil bath and HCN was delivered with 12 cc/min. nitrogen flow rate. After 180 minutes, GC indicated 93.9% conversion to dinitrile with ADN selectivity of 88.4%.

Example 19

Aspect 7: Preparation of polymeric phosphorochloridite: A 200 mL round bottom flask was charged with 8.716 g of 2,2-bis(4-hydroxy-3-methylphenyl)propane, 3.077 g of acryloyl chloride, and 80 mL of THF. The mixture was cooled to −30° C. and a precooled (−30° C.) solution of triethylamine (3.643 g) in 20 mL of THF was added. The mixture was stirred at room temperature for 45 minutes and then cooled back to −30° C. To this mixture was added 7.106 g of the phosphorodichloridite of o-cresol in 20 mL of THF and then a precooled solution (−30° C.) of triethylamine (3.9 g) in 25 mL of THF. After stirring at room temperature for 45 minutes, $^{31}$P NMR indicated peaks at 157.16 and 157.14 ppm and small peaks at 126.73 and 126.46 ppm. The solution was filtered and the total volume was adjusted to 150 mL by addition of THF.

The solvent from 10 mL of the solution was removed by vacuum and the residue was vacuum dried. The residue was dissolved in 0.5 mL of toluene and 10 mg of Vazo 64 free radical initiator was added. The mixture was heated at 70° C. for 3 hours. The solid was crushed and heated at 70° C. for another hour. The toluene was removed by vacuum and the solid was vacuum dried overnight. The solid was washed with diethyl ether and dried under vacuum to give 807 mg of brown solid.

Example 19A

Aspect 7: Polymerization of Polymeric Phosphite:

A vial was charged with 0.750 g of the polymeric phosphorochloridite prepared in Example 19, 210 mg of 3,3',5,5',6,6'-hexamethyl-2,2'-dihydroxy-1,1'-biphenyl and 10 mL of THF. To this mixture was added 0.800 g of tri(n-butylamine) and the mixture was stirred overnight. The solvent was removed by vacuum and acetonitrile was added. The solid was filtered and washed with acetonitrile to give 770 mg of pale beige solid. Elemental analysis: 3.16% P.

Example 19B

Aspect 9: Preparation of catalyst: To 0.560 g of the polymeric phosphite prepared in Example 19A was added 5 mL of THF. The mixture was stirred overnight and another 1 mL of THF was added. To the mixture was added 0.052 g of Ni(COD)$_2$, giving an orange slurry. After stirring at room temperature for four hours, the solvent was removed by vacuum and the residue vacuum dried for three hours. To the residue was added 5 mL of 3PN and the solid was filtered, washed successively with acetonitrile, 3PN, and acetonitrile, vacuum dried to give 593 mg of orange solid.

Example 19C

Aspect 10: Hydrocyanation of butadiene: To 16 mg of catalyst prepared as described in Example 19B was added 1.045 mL of a solution containing butadiene and HCN (prepared by mixing 6.734 g of valeronitrile, 6.572 g of 3-pentenenitrile, 5.476 g of butadiene, and 2.187 g of HCN). The mixture was heated at 80° C. for 2 hours. GC indicated 82% conversion to nitriles with 3PN/2M3BN of 1.9.

Example 19D

Aspect 11: Isomerization of 2-methyl-3-butenenitrile: To 16 mg of catalyst prepared as described in Example 19C was added 0.266 mL of a solution containing 2M3BN in valeronitrile (prepared by mixing 20.7 g 2M3BN and 1.8 g of valeronitrile). The mixture was heated to 100° C. for one hour. GC indicated 3PN/2M3BN ratio of 10.1.

Having thus described and exemplified the invention with a certain degree of particularity, it should be appreciated that the following claims are not to be so limited but are to be afforded a scope commensurate with the wording of each element of the claim and equivalents thereof.

What is claimed is:

1. A method for making a polymeric, phosphorus-containing composition by heating, in the presence of an initiator, and, optionally in the presence of a Group VIII transition metal, a composition comprising at least one compound of Formula I and/or at least one compound of Formula II,

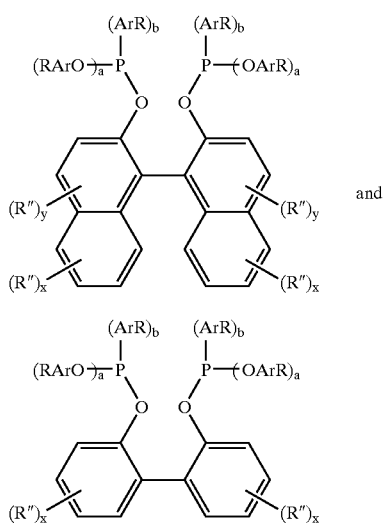

wherein:

$x=0$ to 4;

$y=0$ to 2;

a and b are individually either 0, 1, or 2, provided $a+b=2$;

each Ar is individually selected from the group consisting of phenyl, substituted phenyl, naphthyl, and substituted naphthyl, provided that the two Ar groups that are directly or indirectly bonded to the same phosphorus atom may be linked to each other by a linking unit selected from the group consisting of direct bond, alkylidene, secondary or tertiary amine, oxygen, sulfide, sulfone, and sulfoxide;

each Ar can be further substituted with $C_1$ to $C_{20}$ branched or straight chain alkyl, $C_1$ to $C_{20}$ cycloalkyl, $C_6$ to $C_{20}$ aryl, acetal, ketal, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether;

each R is individually selected from the group consisting of hydrogen, ethenyl, propenyl, acryloyl, methacryloyl and an organic radical with a terminal ethenyl, propenyl, acryloyl, or methacryloyl group;

each R" is individually selected from the group consisting of hydrogen, linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl, cyclic ether, ethenyl, propenyl, and an organic radical with a terminal ethenyl or propenyl group;

provided at least one R represents ethenyl, propenyl, acryloyl, methacryloyl or the organic radical with a terminal ethenyl, propenyl, acryloyl, or methacryloyl group or at least one R" represents ethenyl, propenyl, or the organic radical with a terminal ethenyl or propenyl group, at atmospheric pressure and a temperature between 20° C. and 150° C. for 1 to 100 hours to produce the polymeric composition.

2. The method of claim 1 wherein the initiator is a free radical initiator.

3. A polymeric, phosphorus-containing composition made by the process of claim 1.

* * * * *